United States Patent
Liu et al.

(10) Patent No.: US 8,754,050 B2
(45) Date of Patent: Jun. 17, 2014

(54) MACROCYCLIC COMPOUNDS USEFUL AS INHIBITORS OF HISTONE DEACETYLASES

(75) Inventors: Xuedong Liu, Niwot, CO (US); Andrew J. Phillips, Guilford, CT (US); Dana Ungermannova, Houston, TX (US); Christopher G. Nasveschuk, Stoneham, MA (US); Gan Zhang, Niwot, CO (US)

(73) Assignee: The Regents of the University of Colorado, Denver, CO (US)

( * ) Notice: Subject to any disclaimer, the term of this patent is extended or adjusted under 35 U.S.C. 154(b) by 0 days.

(21) Appl. No.: 13/700,373

(22) PCT Filed: May 26, 2011

(86) PCT No.: PCT/US2011/038246
§ 371 (c)(1),
(2), (4) Date: Mar. 20, 2013

(87) PCT Pub. No.: WO2011/150283
PCT Pub. Date: Dec. 1, 2011

(65) Prior Publication Data
US 2013/0203681 A1    Aug. 8, 2013

Related U.S. Application Data

(60) Provisional application No. 61/348,978, filed on May 27, 2010.

(51) Int. Cl.

| | | |
|---|---|---|
| A61K 38/12 | (2006.01) | |
| A61K 38/06 | (2006.01) | |
| A61K 38/07 | (2006.01) | |
| A61K 39/395 | (2006.01) | |
| C07K 11/00 | (2006.01) | |
| C07K 11/02 | (2006.01) | |

(52) U.S. Cl.
CPC ............ A61K 39/3955 (2013.01); C07K 11/00 (2013.01); C07K 11/02 (2013.01)
USPC ........................................ 514/21.1; 514/21.9

(58) Field of Classification Search
CPC ..... A61K 39/3955; C07K 11/02; C07K 11/00
See application file for complete search history.

(56) References Cited

U.S. PATENT DOCUMENTS

| | | | |
|---|---|---|---|
| 2006/0128660 A1 | 6/2006 | Rajski et al. | |
| 2010/0029731 A1 * | 2/2010 | Williams et al. | 514/366 |

FOREIGN PATENT DOCUMENTS

| | | |
|---|---|---|
| JP | 03-141296 | 6/1991 |
| WO | 2009126315 A2 | 10/2009 |

OTHER PUBLICATIONS

Chinese Office Action in corresponding Chinese Patent Application No. 201180030608.3, mailed Sep. 3, 2013.
International Search Report in corresponding PCT Application No. US2011/38246, mailed Sep. 12, 2011.
Ueda et al., "Action of FR901228, a Novel Antitumor Bicyclic Depsipeptide Produced by *Chromobacterium violaceum* No. 968. on Ha-ras Transformed NIH3T3 Cells", Bioscience, Biotechnology and Biochemistry, 58(9): 1579-1583 (1994).
Allfrey et al., "Acetylation and Methylation of Histones and Their Possible Role in the Regulation of RNA Synthesis", Proc. Natl. Acad. Sci. USA, 51:786-794 (1964).
Benelkebir et al., "Total synthesis of largazole and analogues: HDAC inhibition, antiproliferative activity and metabolic stability", Bioorganic & Medicinal Chemistry, 19:3650-3658 (2011).
Berge et al., "Pharmaceutical salts", Journal of Pharmaceutical Sciences, 66(1):1-19 (1977).
Bowers et al., "Total Synthesis and Biological Mode of Action of Largazole: a Potent Class I Histone Deacetylase Inhibitor". J. Am. Chem. Soc., 130(33):11219-11222 (2008).
Finnin et al., "Structures of a histone deacetylase homologue bound to the TSA and SAHA inhibitors", Nature, 401:188-193 (1999).
Furumai et al., "FK228 (depsipeptide) as a natural prodrug that inhibits class I histone deacetylases", Cancer Res., 62(17):4916-4921 (2002).
Ghosh et al., "Enantioselective total synthesis of ( + )-largazole, a potent inhibitor of histone deacetylase", Org. Lett., 10(17):3907-3909 (2008).
Hang et al., "Chemoselective approaches to glycoprotein assembly", Accounts of Chemical Research, 34(9)727-736 (2001).
Hong et al., "Largazole: From discovery to broad-spectrum therapy", Nat. Prod. Rep., 29:449-456 (2012).
Kiick et al., "Incorporation of azides into recombinant proteins for chemoselective modification by the Staudinger ligation", Proc. Natl. Acad. Sci. USA, 99(1):19-24 (2002).
Kim et al., "Histone deacetylase in carcinogenesis and its inhibitors as anticancer agents", J. Biochem. Mol. Biol., 36(1):110-119 (2003).
Lane et al., "Histone deacetylase inhibitors in cancer therapy", J. Clin. Oncol., 27(32):5459-5468 (Nov. 10, 2009).

(Continued)

Primary Examiner — Marcela M Cordero Garcia
Assistant Examiner — Kaipeen Yang
(74) Attorney, Agent, or Firm — Morgan, Lewis & Bockius LLP

(57) ABSTRACT

The present invention provides a novel macrocyclic compound of general Formula (I) having histone deacetylase (HDAC) inhibitory activity, a pharmaceutical composition comprising the compound, and a method useful to treat diseases using the compound.

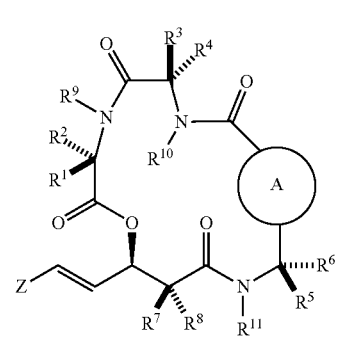

13 Claims, 10 Drawing Sheets

(56) References Cited

OTHER PUBLICATIONS

Leder et al., "Differentiation of erythroleukemic cells in the presence of inhibitors of DNA synthesis", Science, 190(4217):893-894 (1975).
Lemieux et al., "Chemoselective ligation reactions with proteins, oligosaccharides and cells". Trends in Biotechnology, 16(12):506-513 (1998).
Marks, P. A., "The clinical development of histone deacetylase inhibitors as targeted anticancer drugs", Expert Opin. Investig. Drugs, 19(9):1049-1066 (2010).
Marks et al., "Dimethyl sulfoxide to vorinostat: development of this histone deacetylase inhibitor as an anticancer drug", Nat. Biotechnol., 25(1):84-90 (2007).
Masuoka et al., "Phoenistatin, a new gene expression-enhancing substance produced by *Acremonium fusigerum*", J. Antibiot. (Tokyo), 54(2):187-190 (2001).
Minucci et al., "Histone deacetylase inhibitors and the promise of epigenetic (and more) treatments for cancer", Nat. Rev. Cancer, 6(1):38-51 (2006).
Nasveschuk et al., "A Concise Total Synthesis of Largazole, Solution Structure, and Some Preliminary Structure Activity Relationships". Org. Lett., 10(16):3595-3598 (2008).
Newkirk et al., "Discovery, biological activity, synthesis and potential therapeutic utility of naturally occurring histone deacetylase inhibitors", Nat. Prod. Rep., 26(10):1293-1320 (2009).
Rautio et al., "Prodrugs: design and clinical applications", Nat. Rev. Drug. Discov., 7(3):255-270 (2008).
Sato et al., "Ultrastructural changes in Friend erythroleukemia cells treated with dimethyl sulfoxide", Cancer Res., 31(10):1402-1417 (1971).
Seiser et al., "Synthesis and biological activity of largazole and derivatives", Angew. Chem. Int. Ed. Engl., 47(34):6483-6485 (2008).
Shigematsu et al., "FR901228, a novel antitumor bicyclic depsipeptide produced by *Chromobacterium violaceum* No. 968. II. Structure determination", J. Antibiot. (Tokyo), 47(3):311-314 (1994).
Somoza et al., "Structural snapshots of human HDAC8 provide insights into the class I histone deacetylases", Structure, 12(7):1325-1334 (2004).
Taori et al., "Structure and activity of largazole, a potent antiproliferative agent from the Floridian marine *Cyanobacterium* Symploca sp.", J. Am. Chem. Soc., 130(6):1806-1807 (2008).
Ueda et al., "FR901228, a novel antitumor bicyclic depsipeptide produced by *Chromobacterium violaceum* No. 968. III. Antitumor activities on experimental tumors in mice", J. Antibiot. (Tokyo), 47(3):315-323 (1994).
Ungermannova, D., "P27 as a Molecular Target for Cancer Therapeutics: Discovering Small Molecule Inhibitors of P27 Proteolysis and Structure-Activity Relationship and Mechanistic Studies of Largazole, A Potent Inhibitor of Histone Deacetylase", Ph.D. thesis., University of Colorado-Boulder, Boulder, Colo., USA (2010).
Vannini et al., "Crystal structure of a eukaryotic zinc-dependent histone deacetylase, human HDAC8, complexed with a hydroxamic acid inhibitor"; Proc. Natl. Acad. Sci. USA. 101(42):15064-15069 (2004).
Wolff. M.E., "Burger's medicinal chemistry and drug discovery", 5th Edition, vol. 1: Principles and Practice. Manfred E. Wolff (ed.), Wiley-Interscience, New York. 172-178, 931-932 (1995).
Ying et al., "Synthesis and activity of largazole analogues with linker and macrocycle modification", Org. Lett., 10(18):4021-4024 (2008).
Ying et al., "Total Synthesis and Molecular Target of Largazole, a Histone Deacetylase Inhibitor". J. Am. Chem. Soc., 130(26):8455-8459 (2008).
Zeng et al., "Total synthesis and biological evaluation of largazole and derivatives with promising selectivity for cancer cells", Org. Lett., 12(6):1368-1371 (2010).
Bhansali et al., "Largazole and Analogues with Modified Metal-Binding Motifs Targeting Histone Deacetylases: Synthesis and Biological Evaluation", Journal of Medicinal Chemistry, 54:7453-7463(2011).
Cossy et al., "Cross-metathesis reaction. Generation of highly functionalized olefins from unsaturated alcohols". Journal of Organometallic Chemistry, 624:327-332 (2001).
Dai et al., "Total Synthesis of Largazole". Synlett., No. 15, pp. 2379-2383 (2208).
Gonzalez et al., "Asymmetric Acetate Aldol Reactions in Connection with an Enantioselective Total Synthesis of Macrolactin A", Tetrahedron Letters, 37(49):8949-8952 (1996).
Hodge et al., "Stereoselective aldol additions of titanium enolates of N-acetyle-4-isopropyl-thiazolidinethione", Tetrahedron, 60:9397-9403 (2004).
Osorio-Lozada et al., "Indene-Based Thiazolidinethione Chiral Auxiliary for Propionate and Acetate Aldol Additions", Organic Letters, 10(4):617-620 (2008).
Sirasani et al., "Sequencing cross-metathesis and non-metathesis reactions to rapidly access building blocks for synthesis", Tetrahedron, 67:2197-2205 (2011).
Smith III, et al., "Total Synthesis of the Marine Natural Product (−)-Clavosolide A. A Showcase for the Petasis-Ferrier Union/Rearrangement Tactic", Organic Letters, 8(15):3315-3318 (2006).
Souto et al., Synthesis and Biological Characterization of the Histone Deacetylase Inhibitor Largazole and C7-Modified Analogues: J. Med. Chem., 53:4654-4667 (2010).
Voigtritter et al., "Rate Enhanced Olefin Cross-Metathesis Reactions: The Copper Iodide Effect", j. Org. Chem., 76:4697-4702 (2011).
Xiao et al., "Concise total synthesis of largazole", Journal of Asian Natural Products Research, 12(11):940-949 (Nov. 8, 2010).

* cited by examiner

MACROCYCLIC COMPOUNDS USEFUL AS INHIBITORS OF HISTONE DEACETYLASES

RELATED APPLICATIONS

This application claims priority to U.S. Provisional Application Ser. No. 61/348,978, filed May 27, 2010, which is incorporated herein by reference in its entirety.

STATEMENT OF RIGHTS TO INVENTIONS MADE UNDER FEDERALLY SPONSORED RESEARCH

This invention was made with government support under R01 CA 107098 and R01 CA110246 awarded by National Institute of Health. The government has certain rights in the invention.

FIELD OF THE INVENTION

The present disclosure relates generally to a series of novel macrocyclic depsipeptide compounds, having histone deacetylase (HDAC) inhibition properties. In particular, the present disclosure describes compounds that are suitable for use in selectively arresting cell growth, inducing terminal differentiation and/or initiating apoptosis of neoplastic cells thus inhibiting their proliferation. The disclosure describes methods of making these novel macrocyclic compounds, pharmaceutical compositions and methods of treatment comprising selective inhibition HDAC isoforms, resulting in targeted therapies for cancer. Compounds of the invention may also be useful in treating diseases driven by HDAC disregulation such as inflammatory diseases, auto immune diseases, allergic diseases and various diseases of the central nervous system.

BACKGROUND OF THE INVENTION

Largazole, a cyclic depsipeptide originally isolated from a marine cyanobacterium Symploca sp., has been shown to be an anti-tumor agent (Taori et al. 2008). Largazole specifically targets histone deacetylases whose dysfunction is often associated with a variety of human tumors. Largazole has been shown to: (i) display nM $GI_{50}$ values against a variety of cell lines (eg MDA-MB-231 mammary carcinoma cells, $GI_{50}$=7.7 nM; U2OS fibroblastic osteosarcoma cells, $GI_{50}$=55 nM; HT29 colon cells, $GI_{50}$=12 nM; IMR-32 neuroblastoma cells (Taori et al. 2008), $GI_{50}$=16 nM) (Taori et al. 2008), (ii) display differential activity between transformed and non-transformed cells (Nasveschuk et al. 2008; Taori et al. 2008; Ungermannova 2010) and (iii) is structurally simpler and possibly more tractable synthetically than the other depsipeptides.

Although, the largazole molecule is a proven antitumor agent, there is always a need for improved structural analogs that lead to improved HDAC inhibition properties, toxicity and physiochemical profiles resulting is improved cancer therapies.

It has been known for years that DMSO and butyrate, two known relatively nonspecific inhibitors of HDACs, can induce certain leukemia cells to differentiate and suppress neoplastic growth (Sato et al. 1971; Leder et al. 1975).

In recent years, HDACs and histone acetylases (HATs) have become widely recognized as key players in regulating transcription (Minucci and Pelicci 2006). Acetylation of lysines in the histone H3 and histone H4 tails is strongly correlated to chromatin states that are ready for transcription, or that are part of actively transcribed genomic regions (Allfrey et al. 1964). Acetylation of histones has also been correlated with other important cellular functions including chromatin assembly, DNA repair, and recombination.

There are 18 HDAC enzymes in the human genome that can be classified into four classes (Lane and Chabner 2009). Classes I, II and IV all contain a zinc ($Zn^{2+}$) molecule in their active site (Table 1 adapted from (Lane and Chabner 2009)).

Because of their important role in regulating transcription and disruptions of their regulation in tumor cells, it has been postulated that inhibition o HDAC could be an effective way for cancer therapeutics. Consequently, there has been substantial development in inhibitors of HDAC enzymes (HDACi) as potential anti-cancer drugs (Marks). The clinical relevance of this attention to HDACi is warranted and has recently been underscored by the introduction of vorinostat (Zolinza™, Merck, also widely known as SAHA= suberoylanilide hydroxamic acid) for the treatment of cutaneous T-cell lymphoma in late 2006 and more recently Romidepsin (FK228) (Marks).

The catalytic activity of HDAC contains features from both serine protease and metalloprotease enzymes. On the basis of the crystal structures of HDAC8 and a bacterial histone deacetylase-like protein (HDLP), the mechanism for the deacetylation reaction has been proposed (Finnin et al. 1999; Somoza et al. 2004; Vannini et al. 2004). There is a deep, tube-like narrow pocket that expands at the bottom and an internal cavity that borders the pocket (FIG. 1.1). The inside of the tube is comprised of hydrophobic and aromatic residues. The zinc ion is situated at the bottom of the pocket and Zn2+ and His 142, acting as a general base, activate the water molecule for nucleophilic attack on the carbonyl group of the substrate. This would result in a tetrahedral carbon that is stabilized by the formation of a hydrogen bond with Tyr 306 and a general acid His 143 that protonates the lysine leaving group, yielding the acetate and lysine products. Both His 142 and His 143 fit in the Asp 166-His 131 charge-relay system, which is proposed to modulate the basicity of the His residues (FIG. 1.4) (Finnin et al. 1999).

The mode of action of a majority of HDAC inhibitors is to mimic the substrate interactions with the deacetylase, thus preventing the entry of the acetylated lysine residue located on the tail of the histone protein. All small molecule histone deacetylase inhibitors share three structural elements that contribute to HDAC inhibition: (1) a surface recognition domain which is anchored at the rim of the HDAC's tube-like pocket, (2) a zinc binding site, (3) a linker region that connects the surface recognition domain to the zinc binding site (Finnin et al., 1999). FIG. 1.5 (adapted form (Newkirk et al. 2009)) shows a general pharmacophore model of several known HDAC inhibitors.

While SAHA exerts its anti-cancer activity at least in part by the modulation of HDACs in a direct fashion by coordination of the $Zn^{2+}$ ion in the active site of the enzyme by the terminal hydroxamic acid, it displays poor selectivity among the 3 classes of HDACs in part due to its structure simplicity (Minucci and Pelicci 2006; Lane and Chabner 2009). It has been generally accepted that Class I HDACs are more relevant to cancer therapy and poor selectivity of HDAC inhibitors are responsible for chronic toxicities (Minucci and Pelicci 2006; Lane and Chabner 2009). In search for more specific Class I HDAC inhibitors has led to the discovery of a number of natural product depsipeptides including FR901375 (Koho 1991), FK228 (Ueda et al. 1994a), spiruchostatin A (Masuoka et al. 2001), and the very recently isolated largazole (Taori et al. 2008) (FIG. 2). These natural products known as Depsipeptides share a common feature in that they all contain an (3S,4E)-3-hydroxy-7-mercapto-4-heptenoic acid side chain (Newkirk et al. 2009). A free sulfhydryl (thiol) needs to be exposed in this class of compounds to unleash the inhibitory activity of HDAC as the thiol coordinates the active site $Zn^{2+}$ ion to prevent catalysis.

The $Zn^{2+}$ binding moiety of largazole is inactive unless the thioester is removed by hydrolysis. It has been demonstrated that largazole-thiol is the active specie that potently inhibit HDACs (Bowers et al. 2008; Ying et al. 2008b). Thus largazole is most likely a pro-drug that becomes activated by esterase/lipases upon uptake into cells or conjugated to a carrier/transport protein and reduced to thiol intracellularly. There have been significant developments in prodrug design to improve physicochemical and pharmacokinetic properties of biologically potent lead compounds (Rautio et al. 2008). However, these strategies have not been systematically applied to largazole.

SUMMARY OF THE EMBODIMENTS

This invention is related to the field of cancer therapy. In particular, the invention describes novel macrocyclic compounds and pharmaceutical compositions comprising them. Further, the invention describes a novel process for making and using these compounds. These macrocyclic compounds are HDAC inhibitors and are useful as antiproliferation agents for cancer therapy. The methods described herein have identified compounds that have selectivity in targeting HDACs in anti-cancer therapy. These compounds target HDACs whose dysfunction is often associated with a variety of human tumors (Marks and Breslow 2007).

In one aspect, the present invention provides compounds of Formula (I)

Wherein

"A" is aryl or heteroaryl, optionally substituted with one or more groups selected from $C_1$-$C_{10}$ alkyl, $C_3$-$C_{10}$ cycloalkyl, $C_3$-$C_{10}$ heterocycloalkyl, aryl, heteroaryl, halo, hydroxyl, —CN, —COOH, —$CF_3$, —$OCH_2F$, —$OR_{20}$, —$NR_2OR_{22}$, —$NCOR_2OR_{22}$, —$CONR_2OR_{22}$;

Z is —$(CH_2)_nSR_{12}$;

$R_1$ and $R_2$ are independently H, halo, $C_1$-$C_{10}$ alkyl, $C_3$-$C_{10}$ cycloalkyl, $C_3$-$C_{10}$ heterocycloalkyl, or $R_1$ and $R_2$ together, or one of the $R_1$, $R_2$ with $R_9$ form a $C_3$-$C_{10}$ cycloalkyl, $C_3$-$C_{10}$ heterocycloalkyl, wherein the $C_1$-$C_{10}$ alkyl, $C_3$-$C_{10}$ cycloalkyl and $C_3$-$C_{10}$ heterocycloalkyl are optionally substituted with one or more groups selected from $C_1$-$C_{10}$ alkyl, $C_3$-$C_{10}$ cycloalkyl, $C_3$-$C_{10}$ heterocycloalkyl, aryl, heteroaryl, halo, hydroxyl, —CN, —COOH, —$CF_3$, —$OCH_2F$, —$OR_{20}$, —$NR_2OR_{22}$, —$NCOR_2OR_{22}$, —$CONR_{20}R_{22}$;

$R_3$ and $R_4$ are independently H, halo, $C_1$-$C_{10}$ alkyl, $C_3$-$C_{10}$ cycloalkyl, $C_3$-$C_{10}$ heterocycloalkyl, or $R_3$ and $R_4$ together, or one of the $R_3$, $R_4$ with $R_{10}$ form a $C_3$-$C_{10}$ cycloalkyl, $C_3$-$C_{10}$ heterocycloalkyl, wherein the $C_1$-$C_{10}$ alkyl, $C_3$-$C_{10}$ cycloalkyl and $C_3$-$C_{10}$ heterocycloalkyl are optionally substituted with one or more groups selected from $C_1$-$C_{10}$ alkyl, $C_3$-$C_{10}$ cycloalkyl, $C_3$-$C_{10}$ heterocycloalkyl, aryl, heteroaryl, halo, hydroxyl, —CN, —COOH, —$CF_3$, —$OCH_2F$, —$OR_{20}$, —$NR_{20}R_{22}$, —$NCOR_{20}R_{22}$, —$CONR_2OR_{22}$, —$S(O)_mR_{20}$;

$R_5$ and $R_6$ are independently H, halo, $C_1$-$C_{10}$ alkyl, $C_3$-$C_{10}$ cycloalkyl, $C_3$-$C_{10}$ heterocycloalkyl, or $R_5$ and $R_6$ together, or one of the $R_5$, $R_6$ with $R_{11}$ form a $C_3$-$C_{10}$ cycloalkyl, $C_3$-$C_{10}$ heterocycloalkyl, wherein the $C_1$-$C_{10}$ alkyl, $C_3$-$C_{10}$ cycloalkyl, $C_3$-$C_{10}$ heterocycloalkyl are optionally substituted with one or more groups selected from $C_1$-$C_{10}$ alkyl, $C_3$-$C_{10}$ cycloalkyl, $C_3$-$C_{10}$ heterocycloalkyl, aryl, heteroaryl, halo, hydroxyl, —CN, —COOH, —$CF_3$, —$OCH_2F$, —$OR_D$), —$NR_2OR_{22}$, —$NCOR_2OR_{22}$, —$CONR_2OR_{22}$;

$R_7$ and $R_8$ are independently H, halo, $C_1$-$C_{10}$ alkyl, $C_3$-$C_{10}$ cycloalkyl, $C_3$-$C_{10}$ heterocycloalkyl, or $R_5$ and $R_6$ together form a $C_3$-$C_{10}$ cycloalkyl, $C_3$-$C_{10}$ heterocycloalkyl, wherein the $C_1$-$C_{10}$ alkyl, $C_3$-$C_{10}$ cycloalkyl, $C_3$-$C_{10}$ heterocycloalkyl are optionally substituted with one or more groups selected from $C_1$-$C_{10}$ alkyl, $C_3$-$C_{10}$ cycloalkyl, $C_3$-$C_{10}$ heterocycloalkyl, aryl, heteroaryl, halo, hydroxyl, —CN, —COOH, —$CF_3$, —$OCH_2F$, —$OR_{20}$, —$NR_2OR_{22}$, —$NCOR_2OR_{22}$, —$CONR_{20}R_{22}$;

$R_9$ is independently H, $C_1$-$C_{10}$ alkyl, $C_3$-$C_{10}$ cycloalkyl, $C_3$-$C_{10}$ heterocycloalkyl, or together with one of $R_1$, $R_2$ form a $C_3$-$C_{10}$ cycloalkyl, $C_3$-$C_{10}$ heterocycloalkyl, wherein the $C_1$-$C_{10}$ alkyl, $C_3$-$C_{10}$ cycloalkyl, $C_3$-$C_{10}$ heterocycloalkyl are optionally substituted with one or more groups selected from $C_1$-$C_{10}$alkyl, $C_3$-$C_{10}$ cycloalkyl, $C_3$-$C_{10}$ heterocycloalkyl, aryl, heteroaryl, halo, hydroxyl, —CN, —COOH, —$CF_3$, —$OCH_2F$, —$OR_{20}$, —$NR_{20}R_{22}$, —$NCOR_{20}R_{22}$, —$CONR_{20}R_{22}$;

$R_{10}$ is independently H, $C_1$-$C_{10}$ alkyl, $C_3$-$C_{10}$ cycloalkyl, $C_3$-$C_{10}$ heterocycloalkyl, or together with one of $R_3$, $R_4$ form a $C_3$-$C_{10}$ cycloalkyl, $C_3$-$C_{10}$ heterocycloalkyl, wherein the $C_1$-$C_{10}$ alkyl, $C_3$-$C_{10}$ cycloalkyl, $C_3$-$C_{10}$ heterocycloalkyl are optionally substituted with one or more groups selected from $C_1$-$C_{10}$ alkyl, $C_3$-$C_{10}$ cycloalkyl, $C_3$-$C_{10}$ heterocycloalkyl, aryl, heteroaryl, halo, hydroxyl, —CN, —COOH, —$CF_3$, —$OCH_2F$, —$OR_{20}$, —$NR_2OR_{22}$, —$NCOR_2OR_{22}$, —$CONR_{20}R_{22}$;

$R_{11}$ is independently H, $C_1$-$C_{10}$ alkyl, $C_3$-$C_{10}$ cycloalkyl, $C_3$-$C_{10}$ heterocycloalkyl, or together with one of $R_5$, $R_6$ form a $C_3$-$C_8$ cycloalkyl, $C_3$-$C_8$ heterocycloalkyl, wherein the $C_1$-$C_{10}$alkyl, $C_3$-$C_{10}$ cycloalkyl, $C_3$-$C_{10}$ heterocycloalkyl are optionally substituted with one or more groups selected from $C_1$-$C_8$ alkyl, $C_3$-$C_8$ cycloalkyl, $C_3$-$C_8$ heterocycloalkyl, aryl, heteroaryl, halo, hydroxyl, —CN, —COOH, —$CF_3$, —$OCH_2F$, —$OR_{20}$, —$NR_2OR_{22}$, —$NCOR_{20}R_{22}$, —$CONR_{20}R_{22}$;

$R_{12}$ is independently H, $C_1$-$C_{10}$ alkyl, —$COR_{20}$, —$CONR_2OR_{22}$, —$OR_{20}$, —$COOR_{20}$, —$COCR_2OR_{22}NR_2OR_{22}$, —$SR_{20}$, —$P(O)(OR_{24})_2$;

$R_{20}$ and $R_{22}$ are independently H, $C_1$-$C_{10}$ alkyl, $C_3$-$C_{10}$ cycloalkyl, $C_3$-$C_{10}$ heterocycloalkyl, aryl or heteroaryl;

$R_{24}$ is independently H, $C_1$-$C_{10}$ alkyl, $C_3$-$C_{10}$ cycloalkyl, $C_3$-$C_{10}$ heterocycloalkyl, Na, K or Ca;

n=1-6;
m=1 or 2;
or a pharmaceutically acceptable salt, solvate, prodrug or stereoisomer thereof.

In another aspect, the present invention provides compounds of Formula (II)

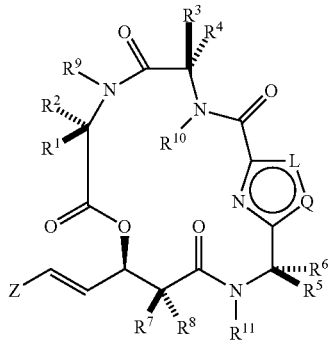

II

Wherein
L and Q are independently S, O, N, or $CR_{26}$
$R_{26}$ is independently H, halo, $C_1$-$C_{10}$ alkyl, $C_3$-$C_{10}$ cycloalkyl, $C_3$-$C_{10}$ heterocycloalkyl, aryl, heteroaryl, wherein the $C_1$-$C_{10}$ alkyl, $C_3$-$C_{10}$ cycloalkyl, $C_3$-$C_{10}$ heterocycloalkyl, aryl and heteroaryl are optionally substituted with one or more groups selected from $C_1$-$C_{10}$ alkyl, $C_3$-$C_{10}$ cycloalkyl, $C_3$-$C_{10}$ heterocycloalkyl, aryl, heteroaryl, halo, hydroxyl, —CN, —COOH, —$CF_3$, —$OCH_2F$, —$OR_{20}$, —$NR_{20}R_{22}$, —$NCOR_{20}R_{22}$, —$CONR_2OR_{22}$;
$R_1$, $R_2$, $R_3$, $R_4$, $R_5$, $R_6$, $R_7$, $R_8$, $R_9$, $R_{10}$, $R_{11}$ and Z are as described above;
or a pharmaceutically acceptable salt, solvate, prodrug or stereoisomer thereof.

In yet another aspect, the present invention provides compounds of Formula (III)

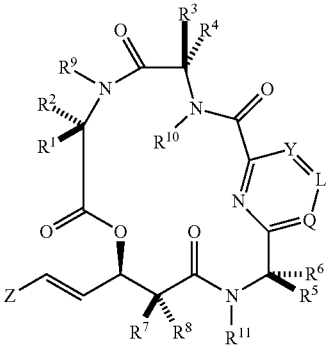

III

Wherein
L, Q and Y are independently S, O, N, or $CR_{26}$;
$R_{26}$ is independently H, halo, $C_1$-$C_{10}$ alkyl, $C_3$-$C_{10}$ cycloalkyl, $C_3$-$C_{10}$ heterocycloalkyl, aryl, heteroaryl, wherein the $C_1$-$C_{10}$ alkyl, $C_3$-$C_{10}$ cycloalkyl, $C_3$-$C_{10}$ heterocycloalkyl, aryl and heteroaryl are optionally substituted with one or more groups selected from $C_1$-$C_{10}$ alkyl, $C_3$-$C_{10}$ cycloalkyl, $C_3$-$C_{10}$ heterocycloalkyl, aryl, heteroaryl, halo, hydroxyl, —CN, —COOH, —$CF_3$, —$OCH_2F$, —$OR_{20}$, —$NR_2OR_{22}$, —$NCOR_{20}R_{22}$, —$CONR_2OR_{22}$;
$R_1$, $R_2$, $R_3$, $R_4$, $R_5$, $R_6$, $R_7$, $R_8$, $R_9$, $R_{10}$, $R_{11}$ and Z are as described above;
or a pharmaceutically acceptable salt, solvate, prodrug or stereoisomer thereof.

In yet another aspect, the present invention provides compound of Formula (IV)

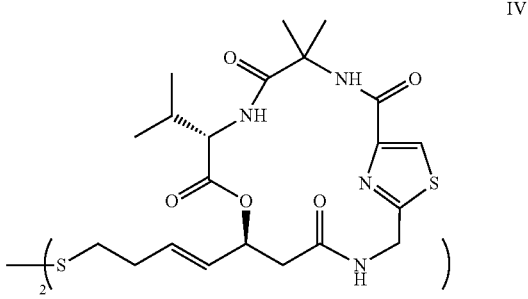

IV or a pharmaceutically acceptable salt, solvate, prodrug or stereoisomer thereof.

In yet another aspect, the present invention provides compound of Formula (V)

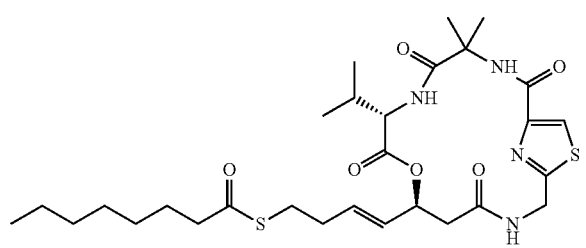

V or a pharmaceutically acceptable salt, solvate, prodrug or stereoisomer thereof.

In yet another aspect, the present invention provides compound of Formula (VI)

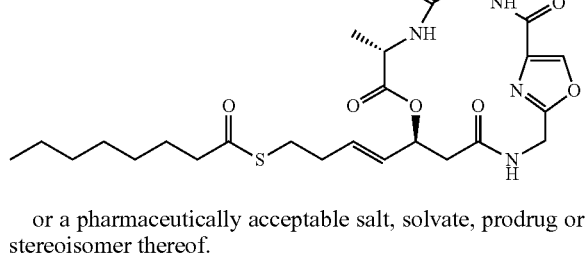

VI or a pharmaceutically acceptable salt, solvate, prodrug or stereoisomer thereof.

In yet another aspect, the present invention provides compound of Formula (VII)

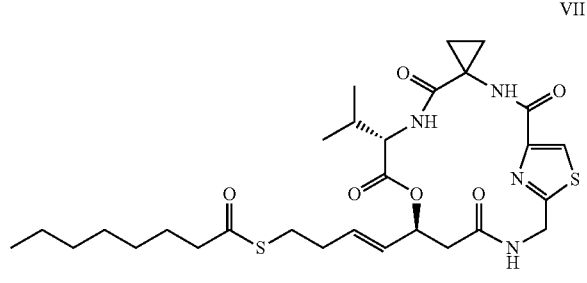 [SMILES: CCCCCCCC(=O)SCC/C=C/[C@@H]1CC(=O)NCc2nc(cs2)C(=O)NC2(CC2)C(=O)N[C@@H](C(C)C)C(=O)O1]

VII or a pharmaceutically acceptable salt, solvate, prodrug or stereoisomer thereof.

In yet another aspect, the present invention provides compound of Formula (VIII)

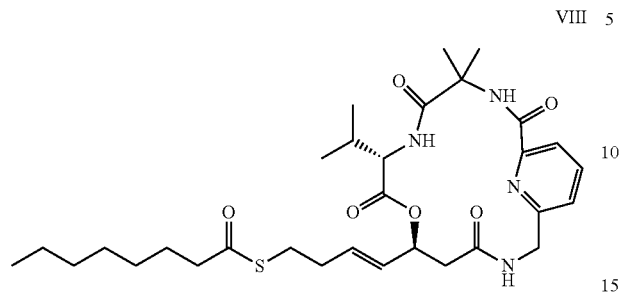

VIII or a pharmaceutically acceptable salt, solvate, prodrug or stereoisomer thereof.

In yet another aspect, the present invention provides compound of Formula (IX)

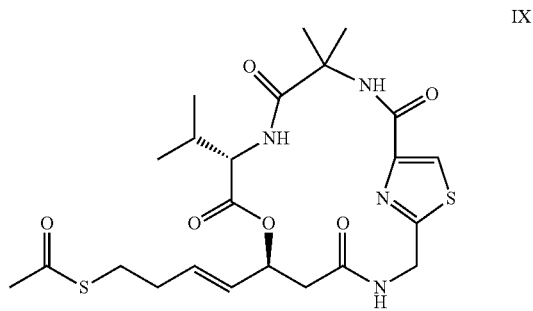 [SMILES: CC(=O)SCC/C=C/[C@@H]1CC(=O)NCc2nc(cs2)C(=O)NC(C)(C)C(=O)N[C@@H](C(C)C)C(=O)O1]

IX or a pharmaceutically acceptable salt, solvate, prodrug or stereoisomer thereof.

In yet another aspect, the present invention provides compound of Formula (X)

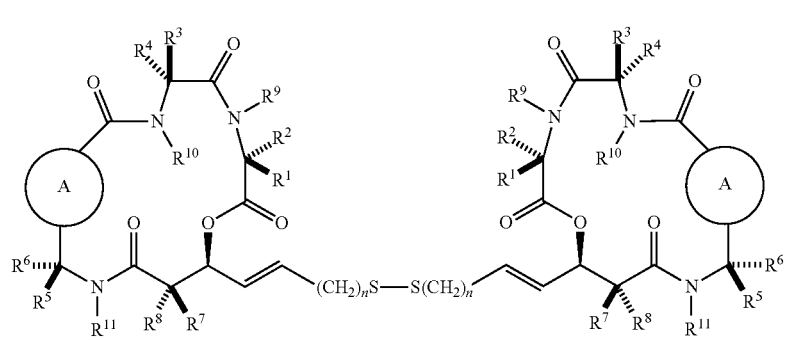

X

Wherein A, $R_1$, $R_2$, $R_3$, $R_4$, $R_5$, $R_6$, $R_7$, $R_8$, $R_9$, $R_{10}$, $R_{11}$ and n are as described above;
or a pharmaceutically acceptable salt, solvate, prodrug or stereoisomer thereof.

In yet another aspect, the present invention provides pharmaceutical compositions of compounds or pharmaceutically acceptable salts of one or more compounds described herein and a pharmaceutically acceptable carrier.

In yet another aspect, the present invention provides methods of treating diseases mediated by HDAC enzymes, comprising administering to a subject in need thereof a therapeutically effective amount of one or more compounds described herein. Other methods involve co-therapies by administering one or more compounds of the present invention with other anti-cancer agents.

b) HCT116 cells respond to largazole, its selective analogues, and SAHA in a dose-dependent fashion. Cells were treated with the indicated compound for 8 hours with concentrations ranging from 1/µM to 100 nM and immunoblotted with anti-acetylhistone H3 antibody. CGN-722, CGN-552 and CGN-596 are slightly more potent deacetylase inhibitors than largazole (L) and SAHA. Conversion of thioester into ketone, (CGN-363), renders the compound inactive with respect to HDAC inhibition.

Figure 9A:
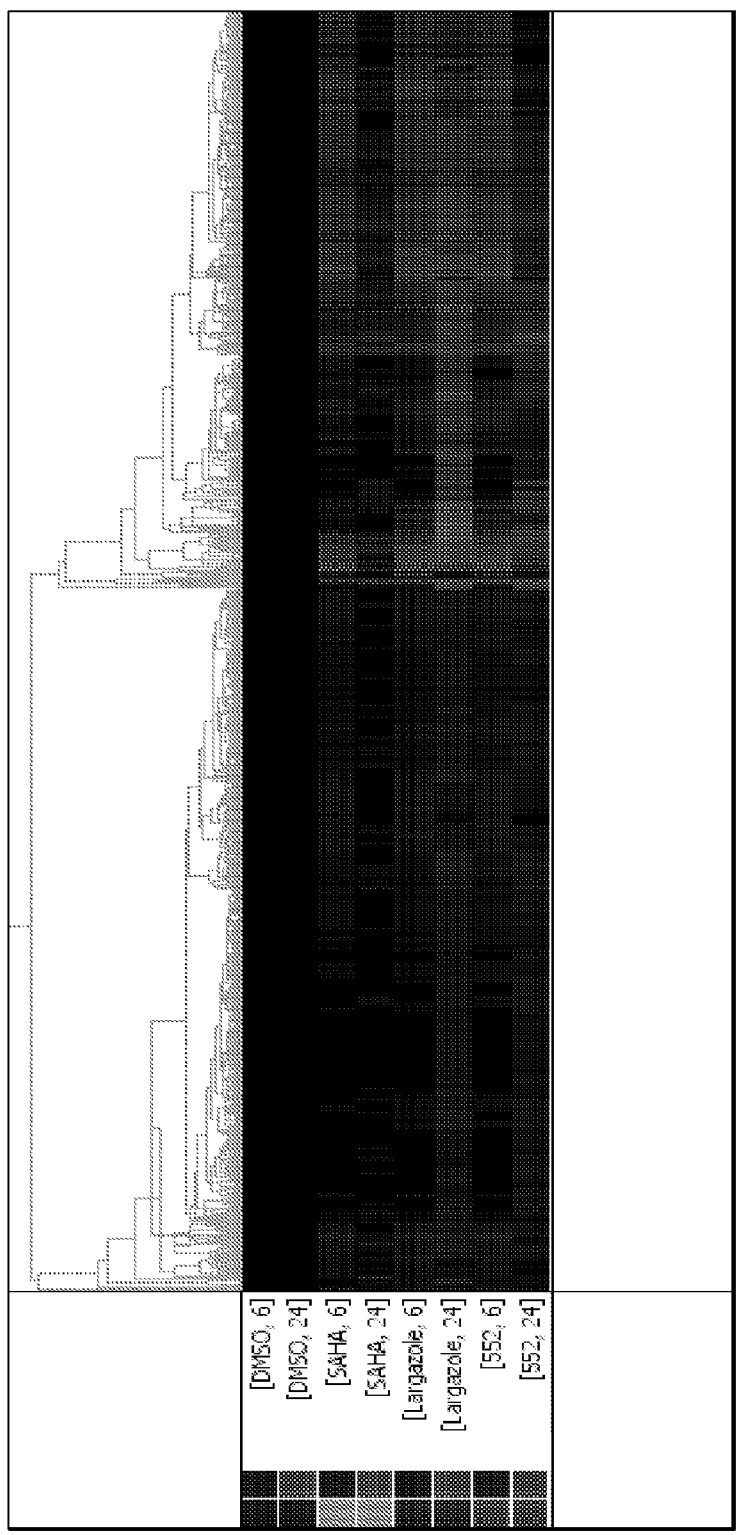
Figure 9C:
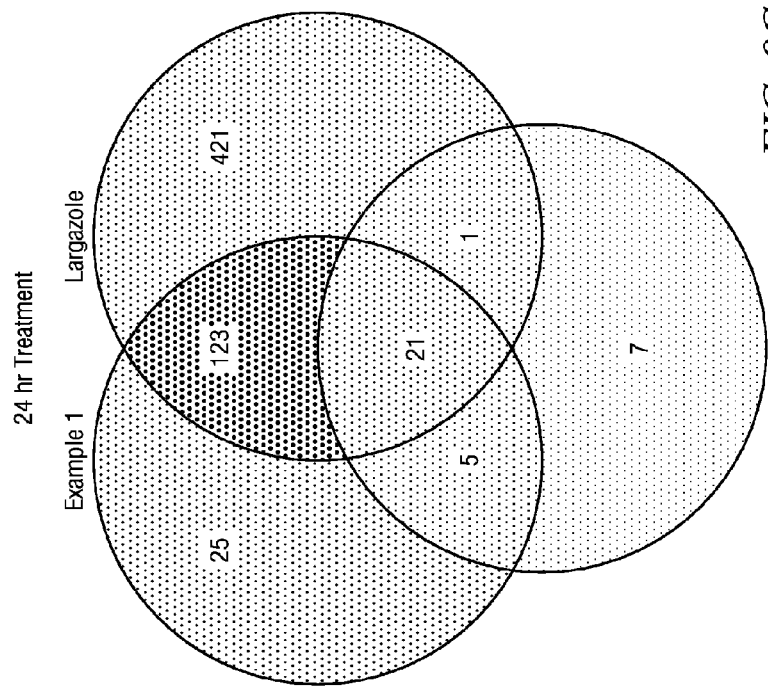
Figure 9B:
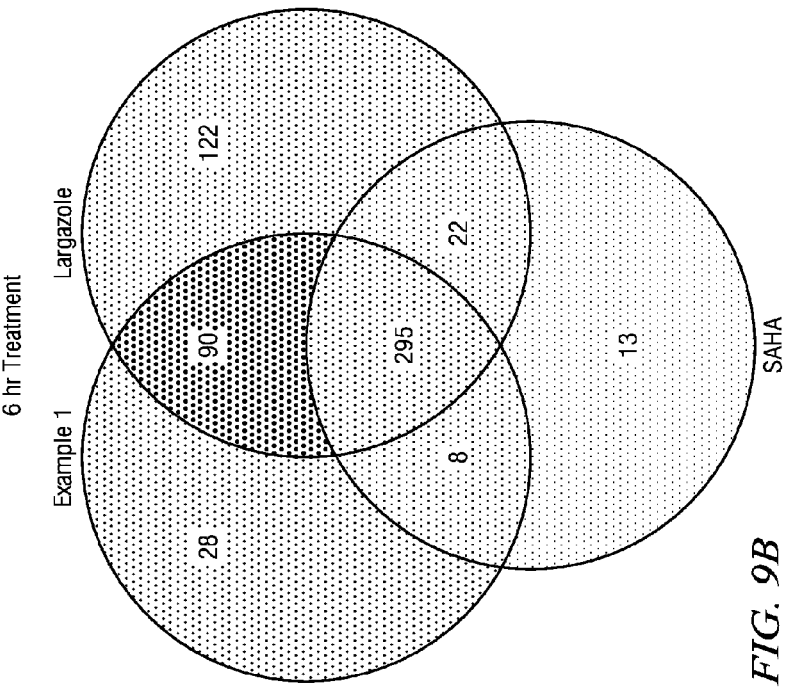

FIG. 9 presents DNA microarray data showing that SAHA, Largazole and its selected analog example 1 cause distinct changes in gene expression profiles in the HCT 116 cancer cell line. a) hierarchical clustering and heatmaps of changes in gene expression profiles in the HCT116 cells with indicated treatment. b) Venn diagrams showing unique and shared gene sets whose expression levels changed by more than 2 fold upon exposure to the indicated treatment at 6 hr and 24 hr.

Table 1 presents classification of HDAC isoforms. Class I consists of HDAC 1, 2, 3, and 8. Class II consists of HDAC 4, 5, 6, 7, 9, 10.

Table 2 presents exemplary data showing an effect of largazole, largazole analogs along with example compounds of present invention on cancer cell growth inhibition.

Comparative analysis of the cytotoxic effect of largazole in human cancer cell lines HCT116, SW480 and MDA-MB231. HME were used as control. 8,000 cells were plated in 96-well plates where rows 1 and 10 were treated with DMSO, row 2 had no cells to establish background levels, rows 3-9 contained decreasing concentrations of compound. Cells were incubated with largazole for 48 hours, followed by staining with crystal violet dye. The absorbance at 588 nM was measured using a Tecan Sail re II plate reader. Experiments were performed in replicates of six, and concentration-response curves were generated by nonlinear least square regression analysis of the data using GraphPad Prism (San Diego, Calif.). The growth inhibition ($GI_{50}$) for each compound was defined as a concentration of drug leading to a 50% reduction in A588 compared with controls Table 3 shows a summary of the number of genes whose expression levels changed by 2 fold upon treatment with indicated chemicals in comparison to DMSO. Expression values files for each sample were generated using the Robust Multichip Average (RMA) algorithm. Differential expression was determined using the R software package limma to generate linear models and empirical Bayesian statistics. Genes were considered differentially expressed if the P value, adjusted for multiple testing using the Benjamini and Hochberg method, was ≤5% and the log-2 fold change was ≤1 or ≥−1.

DETAILED DESCRIPTION

The following description is merely exemplary in nature and is not intended to limit the present disclosure, application, or uses.

DEFINITIONS

The term "substitute for" as used herein, refers to switching the administration of a first compound or drug to a subject for a second compound or drug to the subject. For example, a Kratom extract may be substituted for an addictive compound such that a subject will be administered the Kratom extract instead of the addictive compound.

The term "at risk for" as used herein, refers to a medical condition or set of medical conditions exhibited by a patient which may predispose the patient to a particular disease or affliction. For example, these conditions may result from influences that include, but are not limited to, behavioral, emotional, chemical, biochemical, or environmental influences.

The term "effective amount" as used herein, refers to a particular amount of a pharmaceutical composition comprising a therapeutic agent that achieves a clinically beneficial result (i.e., for example, a reduction of symptoms). Toxicity and therapeutic efficacy of such compositions can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The term "symptom", as used herein, refers to any subjective or objective evidence of disease or physical disturbance observed by the patient. For example, subjective evidence is usually based upon patient self-reporting and may include, but is not limited to, pain, headache, visual disturbances, nausea and/or vomiting. Alternatively, objective evidence is usually a result of medical testing including, but not limited to, body temperature, complete blood count, lipid panels, thyroid panels, blood pressure, heart rate, electrocardiogram, tissue body imaging scans and other medical testing results.

The term "disease", as used herein, refers to any impairment of the normal state of the living animal or one of its parts that interrupts or modifies the performance of the vital functions. Typically manifested by distinguishing signs and symptoms, it is usually a response to: i) environmental factors (as malnutrition, industrial hazards, or climate); ii) specific infective agents (as worms, bacteria, or viruses); iii) inherent defects of the organism (as genetic anomalies); and/or iv) combinations of these factors The terms "reduce," "inhibit," "diminish," "suppress," "decrease," "prevent" and grammatical equivalents (including "lower," "smaller," etc.) when in reference to the expression of any symptom in an untreated subject relative to a treated subject, mean that the quantity and/or magnitude of the symptoms in the treated subject is lower than in the untreated subject by any amount that is recognized as clinically relevant by any medically trained personnel. In one embodiment, the quantity and/or magnitude of the symptoms in the treated subject is at least 10% lower than, at least 25% lower than, at least 50% lower than, at least 75% lower than, and/or at least 90% lower than the quantity and/or magnitude of the symptoms in the untreated subject.

The term "inhibitory compound" as used herein, refers to any compound capable of interacting with (i.e., for example, attaching, binding etc.) to a binding partner under conditions such that the binding partner becomes unresponsive to its natural ligands. Inhibitory compounds may include, but are not limited to, small organic molecules, antibodies, and proteins/peptides.

The term "attached" as used herein, refers to any interaction between a medium (or carrier) and a drug. Attachment may be reversible or irreversible. Such attachment includes, but is not limited to, covalent bonding, ionic bonding, Van der Waals forces or friction, and the like. A drug is attached to a medium (or carrier) if it is impregnated, incorporated, coated, in suspension with, in solution with, mixed with, etc.

The term "drug" or "compound" as used herein, refers to any pharmacologically active substance capable of being administered which achieves a desired effect. Drugs or compounds can be synthetic or naturally occurring, non-peptide, proteins or peptides, oligonucleotides or nucleotides, polysaccharides or sugars.

The term "administered" or "administering", as used herein, refers to any method of providing a composition to a patient such that the composition has its intended effect on the patient. An exemplary method of administering is by a direct mechanism such as, local tissue administration (i.e., for example, extravascular placement), oral ingestion, transdermal patch, topical, inhalation, suppository etc.

The term "patient", as used herein, is a human or animal and need not be hospitalized. For example, out-patients, persons in nursing homes are "patients." A patient may comprise any age of a human or non-human animal and therefore includes both adult and juveniles (i.e., children). It is not intended that the term "patient" connote a need for medical treatment, therefore, a patient may voluntarily or involuntarily be part of experimentation whether clinical or in support of basic science studies.

The term "subject" as used herein refers to a vertebrate, preferably a mammal, more preferably a primate, still more preferably a human. Mammals include, without limitation, humans, primates, wild animals, feral animals, farm animals, sports animals, and pets.

The term "affinity" as used herein, refers to any attractive force between substances or particles that causes them to enter into and remain in chemical combination. For example, an inhibitor compound that has a high affinity for a receptor will provide greater efficacy in preventing the receptor from interacting with its natural ligands, than an inhibitor with a low affinity.

The term "derived from" as used herein, refers to the source of a compound or sequence. In one respect, a compound or sequence may be derived from an organism or particular species. In another respect, a compound or sequence may be derived from a larger complex or sequence.

The term "test compound" as used herein, refers to any compound or molecule considered a candidate as an inhibitory compound.

The term "protein" as used herein, refers to any of numerous naturally occurring extremely complex substances (as an enzyme or antibody) that consist of amino acid residues joined by peptide bonds, contain the elements carbon, hydrogen, nitrogen, oxygen, usually sulfur. In general, a protein comprises amino acids having an order of magnitude within the hundreds.

The term "peptide" as used herein, refers to any of various amides that are derived from two or more amino acids by combination of the amino group of one acid with the carboxyl group of another and are usually obtained by partial hydrolysis of proteins. In general, a peptide comprises amino acids having an order of magnitude with the tens.

The term "pharmaceutically" or "pharmacologically acceptable", as used herein, refer to molecular entities and compositions that do not produce adverse, allergic, or other untoward reactions when administered to an animal or a human.

The term, "pharmaceutically acceptable carrier", as used herein, includes any and all solvents, or a dispersion medium including, but not limited to, water, ethanol, polyol (for example, glycerol, propylene glycol, and liquid polyethylene glycol, and the like), suitable mixtures thereof, and vegetable oils, coatings, isotonic and absorption delaying agents, liposome, commercially available cleansers, and the like. Supplementary bioactive ingredients also can be incorporated into such carriers.

The term, "purified" or "isolated", as used herein, may refer to a peptide composition that has been subjected to treatment (i.e., for example, fractionation) to remove various other components, and which composition substantially retains its expressed biological activity.

The term "sample" as used herein is used in its broadest sense and includes environmental and biological samples. Environmental samples include material from the environment such as soil and water. Biological samples may be animal, including, human, fluid (e.g., blood, plasma and serum), solid (e.g., stool), tissue, liquid foods (e.g., milk), and solid foods (e.g., vegetables). For example, a pulmonary sample may be collected by bronchoalveolar lavage (BAL) which comprises fluid and cells derived from lung tissues. A biological sample may comprise a cell, tissue extract, body fluid, chromosomes or extrachromosomal elements isolated from a cell, genomic DNA (in solution or bound to a solid support such as for Southern blot analysis), RNA (in solution or bound to a solid support such as for Northern blot analysis), cDNA (in solution or bound to a solid support) and the like.

The term "biologically active" refers to any molecule having structural, regulatory or biochemical functions. For example, biological activity may be determined, for example, by restoration of wild-type growth in cells lacking protein activity. Cells lacking protein activity may be produced by many methods (i.e., for example, point mutation and frameshift mutation). Complementation is achieved by transfecting cells which lack protein activity with an expression vector which expresses the protein, a derivative thereof, or a portion thereof.

The term "label" or "detectable label" are used herein, to refer to any composition detectable by spectroscopic, photochemical, biochemical, immunochemical, electrical, optical or chemical means. Such labels include biotin for staining with labeled streptavidin conjugate, magnetic beads (e.g., Dynabeads®), fluorescent dyes (e.g., fluorescein, texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads. Patents teaching the use of such labels include, but are not limited to, U.S. Pat. Nos. 3,817,837; 3,850,752; 3,939,350; 3,996,345; 4,277,437; 4,275,149; and 4,366,241 (all herein incorporated by reference). The labels contemplated in the present invention may be detected by many methods. For example, radiolabels may be detected using photographic film or scintillation counters, fluorescent markers may be detected using a photodetector to detect emitted light. Enzymatic labels are typically detected by providing the enzyme with a substrate and detecting, the reaction product produced by the action of the enzyme on the substrate, and calorimetric labels are detected by simply visualizing the colored label.

The term "conjugate", as used herein, refers to any compound that has been formed by the joining of two or more moieties.

A "moiety" or "group" is any type of molecular arrangement designated by formula, chemical name, or structure. Within the context of certain embodiments, a conjugate is said to comprise one or more moieties or chemical groups. This means that the formula of the moiety is substituted at some place in order to be joined and be a part of the molecular arrangement of the conjugate. Although moieties may be directly covalently joined, it is not intended that the joining of two or more moieties must be directly to each other. A linking group, crosslinking group, or joining group refers any molecular arrangement that will connect the moieties by covalent bonds such as, but are not limited to, one or more amide group(s), may join the moieties. Additionally, although the conjugate may be unsubstituted, the conjugate may have a variety of additional substituents connected to the linking groups and/or connected to the moieties.

A "polymer" or "polymer group" means a chemical species or group made up of repeatedly linked moieties. Within certain embodiments, it is preferred that the number repeating moieties is three or more or greater than 10. The linked moieties may be identical in structure or may have variation of moiety structure. A "monomeric polymer" or "homopolymer" is a polymer that contains the same repeating, asymmetric subunit. A "copolymer" is a polymer that is derived from two or more types of monomeric species, i.e. two or more different chemical asymmetric subunits. "Block copolymers" are polymers comprised of two or more species of polymer subunits linked by covalent bonds.

The term "substituted", as used herein, means at least one hydrogen atom of a molecular arrangement is replaced with a substituent. In the case of an oxo substituent ("=O"), two hydrogen atoms are replaced. When substituted, one or more of the groups below are "substituents." Substituents include, but are not limited to, halogen, hydroxy, oxo, cyano, nitro, amino, alkylamino, dialkylamino, alkyl, alkoxy, alkylthio, haloalkyl, aryl, arylalkyl, heteroaryl, heteroarylalkyl, heterocycle, and heterocyclealkyl, as well as, —NRaRb, —NRaC(=O)Rb, —NRaC(=O)NRaNRb, —NRaC(=O)ORb, —NRaSO$_2$Rb, —C(=O)Ra, —C(=O)ORa, —C(=O)NRaRb, —OC(=O)NRaRb, —OR, —SR, —SORo, —S(=O)aR, —OS(=O)$_2$Ra and —S(=O)ORa. In addition, the above substituents may be further substituted with one or more of the above substituents, such that the substituent comprises a substituted alky, substituted aryl, substituted arylalkyl, substituted heterocycle, or substituted heterocyclealkyl. Ra and Rb in this context may be the same or different and, independently, hydrogen, alkyl, haloalkyl, substituted alkyl, aryl, substituted aryl, arylalkyl, substituted arylalkyl, heterocycle, substituted heterocycle, heterocyclealkyl or substituted heterocyclealkyl.

The term "unsubstituted", as used herein, refers to any compound that does not contain extra substituents attached to the compound. An unsubstituted compound refers to the chemical makeup of the compound without extra substituents, e.g., the compound does not contain protecting group(s). For example, unsubstituted proline is a proline amino acid even though the amino group of proline may be considered disubstituted with alkyl groups.

The term "alkyl", as used herein, means any straight chain or branched, non-cyclic or cyclic, unsaturated or saturated aliphatic hydrocarbon containing from 1 to 10 carbon atoms, while the term "lower alkyl" has the same meaning as alkyl but contains from 1 to 6 carbon atoms. The term "higher alkyl" has the same meaning as alkyl but contains from 2 to 10 carbon atoms. Representative saturated straight chain alkyls include, but are not limited to, methyl, ethyl, n-propyl, n-butyl, n-pentyl, n-hexyl, n-septyl, n-octyl, n-nonyl, and the like; while saturated branched alkyls include, but are not limited to, isopropyl, sec-butyl, isobutyl, tert-butyl, isopentyl, and the like. Cyclic alkyls may be obtained by joining two alkyl groups bound to the same atom or by joining two alkyl groups each bound to adjoining atoms. Representative saturated cyclic alkyls include, but are not limited to, cyclopropyl, cyclobutyl, cyclopentyl, cyclohexyl, and the like; while unsaturated cyclic alkyls include, but are not limited to, cyclopentenyl and cyclohexenyl, and the like. Cyclic alkyls are also referred to herein as a "homocycles" or "homocyclic rings." Unsaturated alkyls contain at least one double or triple bond between adjacent carbon atoms (referred to as an "alkenyl" or "alkynyl", respectively). Representative straight chain and branched alkenyls include, but are not limited to, ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include, but are not limited to, acetylenyl, propynyl, 1-butynyl, 2-butynyl, 1-pentynyl, 2-pentynyl, 3-methyl-1-butynyl, and the like.

The term "aryl", as used herein, means any aromatic carbocyclic moiety such as, but not limited to, phenyl or naphthyl.

The term "arylalkyl", or "aralkyl" as used herein, means any alkyl having at least one alkyl hydrogen atoms replaced with an aryl moiety, such as benzyl, but not limited to, —(CH$_2$)$_2$-phenyl, —(CH$_2$)$_3$-phenyl, —CH(phenyl)$_2$, and the like.

The term "halogen", as used herein, refers to any fluoro, chloro, bromo, or iodo moiety.

The term "haloalkyl", as used herein, refers to any alkyl having at least one hydrogen atom replaced with halogen, such as trifluoromethyl, and the like.

The term "heteroaryl", as used herein, refers to any aromatic heterocycle ring of 5 to 10 members and having at least one heteroatom selected from nitrogen, oxygen and sulfur, and containing at least 1 carbon atom, including, but not limited to, both mono and bicyclic ring systems. Representative heteroaryls include, but are not limited to, furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, or quinazolinyl.

The term "heteroarylalkyl", as used herein, means any alkyl having at least one alkyl hydrogen atom replaced with a heteroaryl moiety, such as —CHpyridinyl, CH$_2$pyrimidinyl, and the like.

The term "heterocycle" or "heterocyclic ring", as used herein, means any 4- to 7-membered monocyclic, or 7- to 10-membered bicyclic, heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles may include heteroaryls exemplified by those defined above. Thus, in addition to the heteroaryls listed above, heterocycles may also include, but are not limited to, morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The term "heterocycloalkyl", as used herein, means any alkyl having at least one alkyl hydrogen atom replaced with a heterocycle, such as —CH$_2$-morpholinyl, and the like.

The term "homocycle" or "cycloalkyl", as used herein, means any saturated or unsaturated (but not aromatic) carbocyclic ring containing from 3-7 carbon atoms, such as, but not limited to, cyclopropane, cyclobutane, cyclopentane, cyclohexane, cycloheptane, cyclohexene, and the like.

The term "alkylamino", as used herein, means at least one alkyl moiety attached through a nitrogen bridge (i.e., —N-(alkyl)N, such as a dialkylamino)) including, but not limited to, methylamino, ethylamino, dimethylamino, diethylamino, and the like.

The term "alkyloxy" or "alkoxy", as used herein, means any alkyl moiety attached through an oxygen bridge (i.e., —O-alkyl) such as, but not limited to, methoxy, ethoxy, and the like.

The term "alkylthio", as used herein, means any alkyl moiety attached through a sulfur bridge (i.e., —S— alkyl) such as, but not limited to, methylthio, ethylthio, and the like The term "alkenyl" means an unbranched or branched hydrocarbon chain having one or more double bonds therein. The double bond of an alkenyl group can be unconjugated or conjugated to another unsaturated group. Suitable alkenyl groups include, but are not limited to vinyl, allyl, butenyl, pentenyl, hexenyl, butadienyl, pentadienyl, hexadienyl, 2-ethylhexenyl, 2-propyl-2-butenyl,4-(2-methyl-3-butene)-pentenyl. An alkenyl group can be unsubstituted or substituted with one or two suitable substituents.

The term "alkynyl" means unbranched or branched hydrocarbon chain having one or more triple bonds therein. The triple bond of an alkynyl group can be unconjugated or conjugated to another unsaturated group. Suitable alkynyl groups include, but are not limited to ethynyl, propynyl, butynyl, pentynyl, hexynyl, methylpropynyl, 4-methyl-1-butynyl, 4-propyl-2-pentynyl-, and 4-butyl-2-hexynyl. Analkynyl group can be unsubstituted or substituted with one or two suitable substituents The term "salts", as used herein, refers to any salt that complexes with identified compounds contained herein. Examples of such salts include, but are not limited to, acid addition salts formed with inorganic acids (e.g. hydrochloric acid, hydrobromic acid, sulfuric acid, phosphoric acid, nitric acid, and the like), and salts formed with organic acids such as, but not limited to, acetic acid, oxalic acid, tartaric acid, succinic acid, malic acid, fumaric acid, maleic acid, ascorbic acid, benzoic acid, tannic acid, pamoic acid, alginic acid, polyglutamic, acid, naphthalene sulfonic acid, naphthalene disulfonic acid, and polygalacturonic acid. Salt compounds can also be administered as pharmaceutically acceptable quaternary salts known by a person skilled in the art, which specifically include the quaternary ammonium salts of the formula —NR,R',R"+Z—, wherein R, R', R" is independently hydrogen, alkyl, or benzyl, and Z is a counter ion, including, but not limited to, chloride, bromide, iodide, alkoxide, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate). Salt compounds can also be administered as pharmaceutically acceptable pyridine cation salts having a substituted or unsubstituted partial formula: wherein Z is a counter ion, including, but not limited to, chloride, bromide, iodide, alkoxide, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate).

As used herein, the term "prodrug" refers to a derivative of a compound that can hydrolyze, oxidize, or otherwise react under biological conditions (in vitro or in vivo) to provide a compound of the invention. Prodrugs may only become active upon some reaction under biological conditions, but they may have activity in their unreacted forms. Examples of prodrugs contemplated herein include, without limitation, analogs or derivatives of compounds of the invention, and/or their salts when salt formation is possible, but in particular, derivatives of zinc binding thiol moiety. Examples of prodrug moieties include substituted and unsubstituted, branched or unbranched lower alkyl ester moieties, (e.g., propionic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), heteroaryl esters (nicotinate ester), substituted (e.g., with methyl, halo, or methoxy substituents) aryl and aryl-lower alkyl esters, amides, lower-alkyl amides, di-lower alkyl amides, and hydroxy amides. Naturally occurring amino acid esters or their enantiomers, dipeptide esters, phosphate esters, methoxyphosphate esters, disulfides and disulfide dimers. Prodrugs and their uses are well known in the art (see, e.g., Berge et al. 1977). Prodrugs can typically be prepared using well-known methods, such as those described in Burger's Medicinal Chemistry and Drug Discovery (Manfred E. Wolff ed. 1995) and (Rautio, 2008).

As used herein, "reactive groups" refer to nucleophiles, electrophiles, or radically active groups, i.e., groups that react in the presence of radicals. A nucleophile is a moiety that forms a chemical bond to its reaction partner (the electrophile) by donating both bonding electrons. Electrophiles accept these electrons. Nucleophiles may take part in nucleophilic substitution, whereby a nucleophile becomes attracted to a full or partial positive charge on an element and displaces the group it is bonded to. Alternatively nucleophiles may take part in substitution of carbonyl group. Carboxylic acids are often made electrophilic by creating succinyl esters and reacting these esters with aminoalkyls to form amides. Other common nucleophilic groups are thiolalkyls, hydroxylalkys, primary and secondary amines, and carbon nucleophiles such as enols and alkyl metal complexes. Other preferred methods of ligating proteins, oligosaccharides and cells using reactive groups are disclosed in (Lemieux and Bertozzi 1998), incorporated herein by reference. In yet another preferred method, one provides reactive groups for the Staudinger ligation, i.e., "click chemistry" with an azide comprising moiety and alkynyl reactive groups to form triazoles. Micheal additions of a carbon nucleophile enolate with an electrophilic carbonyl, or the Schiffbase formation of a nucleophilic primary or secondary amine with an aldehyde or ketone may also be utilized. Other methods of bioconjugation are provided in (Hang and Bertozzi 2001) and (Kiick et al. 2002), both of which are incorporated by reference.

The term "biocompatible", as used herein, refers to any material that does not illicit a substantial detrimental response in the host. There is always concern, when a foreign object is introduced into a living body, that the object will induce an immune reaction, such as an inflammatory response that will have negative effects on the host. In the context of this invention, biocompatibility is evaluated according to the application for which it was designed: for example; a bandage is regarded a biocompatible with the skin, whereas an implanted medical device is regarded as biocompatible with the internal tissues of the body. Preferably, biocompatible materials include, but are not limited to, biodegradable and biostable materials. A substantial detrimental response has not occurred if an implant comprising the material is in close association to its implant site within the host animal and the response is better than a tissue response recognized and established as suitable from a materials provided in an ASTM.

ASTM subcommittee F04.16 on Biocompatibility Test Methods has developed biocompatibility standards for medical and surgical materials and devices. For example, materials that are to be used in contact with the blood stream must be composed of materials that meet hemocompatibilty standards. One of these tests is for damage to red blood cells, which can result in hemolysis that is, rupturing of the cells, as described in F 756 Practice for Assessment of Hemolytic Properties of Materials, incorporated herein by reference.

As used herein, a "bioactive substance" refers to any of a variety of chemical moieties and that binds with a biomolecule such as, but not limited to, peptides, proteins, enzymes, receptors, substrates, lipids, antibodies, antigens, and nucleic acids. In certain preferred embodiments, the bioactive substance is a biomolecule but it not intended that the bioactive substance be limited to biomolecules. In other preferred embodiments, the bioactive substances provide hydrophobic, hydrophilic or electrostatic interactions, such as polycarboxylic acids that are anionic at physiological pH. In other preferred embodiment, the alkaline growth factors (with isoelectric point above 7) are retained via favorable electrostatic interactions by the polycarboxylates, and subsequently released in a controlled and sustained manner.

"Cancer" is a term used for diseases in which abnormal cells divide without control and are able to invade other tissues. There are more than 100 different types of cancer. Most cancers are named for the organ or type of cell in which they start—for example, cancer that begins in the colon is called colon cancer; cancer that begins in basal cells of the skin is called basal cell carcinoma. The main categories of cancer include carcinomas, sarcomas, leukemias, lymphomas and myelomas, and central nervous system cancers. Some common cancer types include, but are not limited to, bladder cancer, breast cancer, colon and rectal cancer, endometrial cancer, kidney (renal cell) cancer, leukemia, lung cancer, melanoma, non-Hodgkin's lymphoma, pancreatic cancer, prostate cancer, skin cancer (non-melanoma), and thyroid cancer. In one embodiment, the cancers contemplated for treatment herein include colon and breast cancers.

The terms "comprises", "comprising", are intended to have the broad meaning ascribed to them in U.S. Patent Law and can mean "includes", "including" and the like.

EMBODIMENTS OF THE INVENTION

In or about January of 2008, largazole was isolated from a cyanobacterium of the genus *Symploca*, and named for its Key Largo location (Luesch et al, University of Florida). The compound demonstrates antiproliferative activity in the transformed mammary epithelial cell line MDA-MB231 with a $GI_{50}$ of 7.7 nM (Taori et al. 2008). In addition, largazole preferentially targets cancer over normal cells, which makes this marine substance an important synthetic target as well as a potentially valuable cancer chemotherapeutic (Taori et al. 2008). The first reported synthesis of largazole was completed by Luesch and co-workers (Ying et al. 2008b), followed by the Phillips group (Nasveschuk et al. 2008), Cramer group (Seiser et al. 2008), Williams group (Bowers et al. 2008), and Ghosh group (Ghosh and Kulkarni 2008). The molecular basis for its anticancer activity has been suggested to be Histone deacetylases (HDAC) inhibition (Ying et al. 2008b).

HDAC inhibitors have been suggested to be a new class of potent anti-cancer agents for the treatment of solid and hematological malignancies. Current inhibitors of HDACs, such as sodium butyrate, Trichostatin A (TSA), suberoylanilide hydroxamic acid (SAHA), FK228, and others may exhibit their anti-tumor effect by regulating genes and their protein products that are required for cell cycle arrest, DNA damage repair, free radical scavenging and apoptosis (Marks 2010). For example, SAHA has been approved for the treatment of advanced cutaneous T-cell lymphoma (Marks 2007). Several other HDAC inhibitors are presently in clinical trials for cancer treatment (Marks 2010).

Figure 1A:
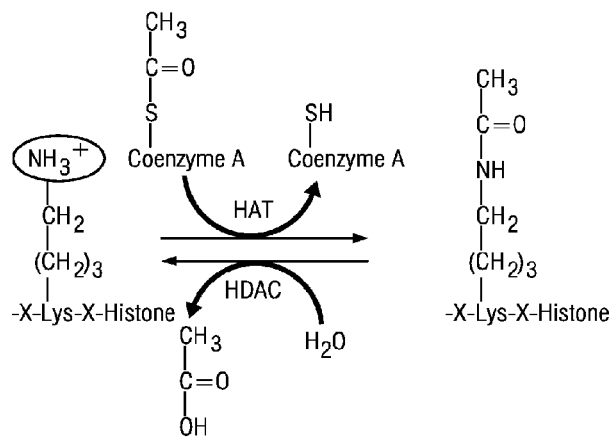
FIG. 1 illustrates a potential role of HAT and HDAC in transcriptional regulation.
A) Histone modification by HAT and HDAC.
B) Regulation of gene expression switches by co-activator or co-repressor complex. Figure and description adapted from (Kim et al. 2003).
Figure 1B:
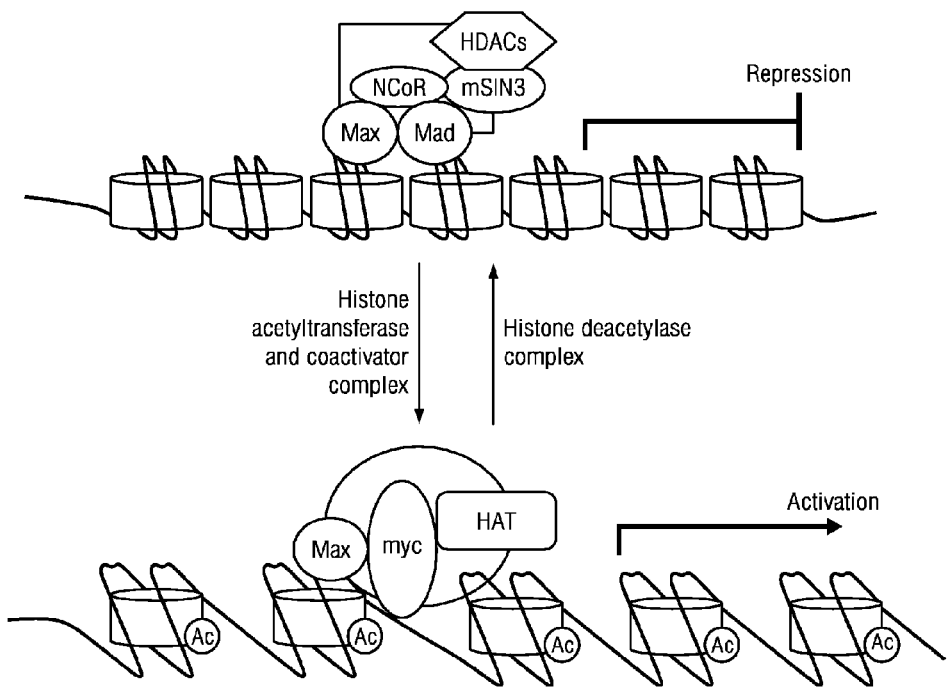
Figure 2A:
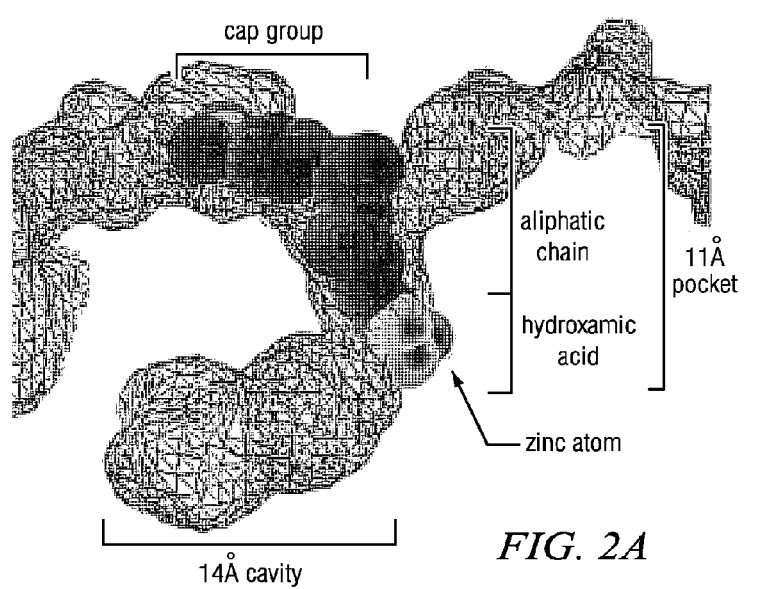
FIG. 2 presents several embodiments of HDLP-TSA complexes.
A) Space-filling representation of TSA in the active-site pocket. The hydroxamic acid group, most of the aliphatic chain and part of the dimethylamino-phenyl group of TSA are buried (60% of TSA's surface area).
B) Schematic representation of HDLP-TSA interactions. Both panels and partial description was adapted from (Finnin et al. 1999).
Figure 2B:
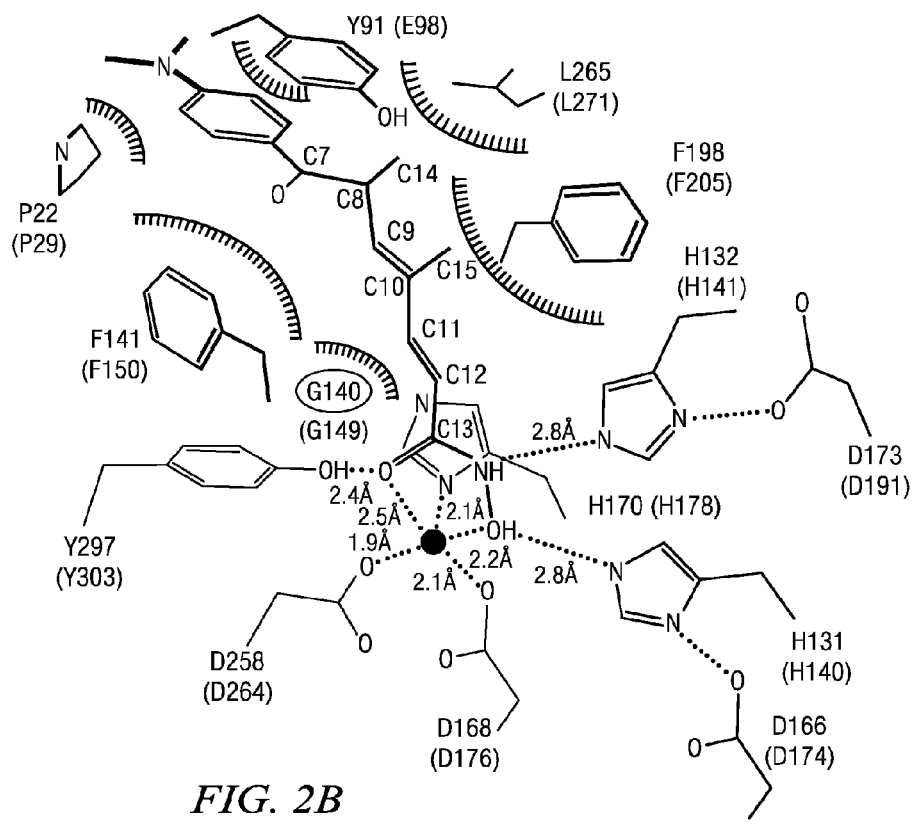
Figure 3:
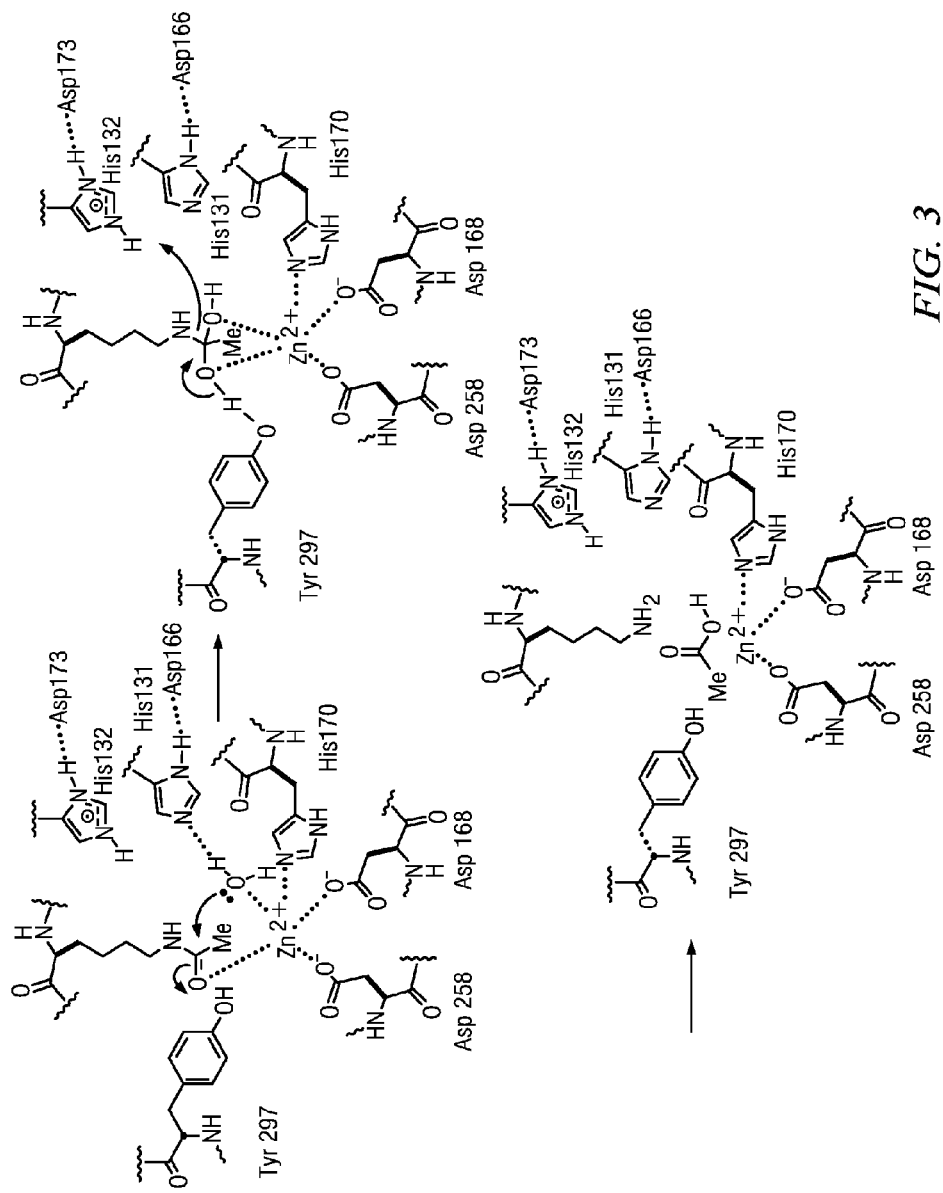
FIG. 3 presents a proposed mechanism of action of zinc-dependent HDACs.
Figure 4:
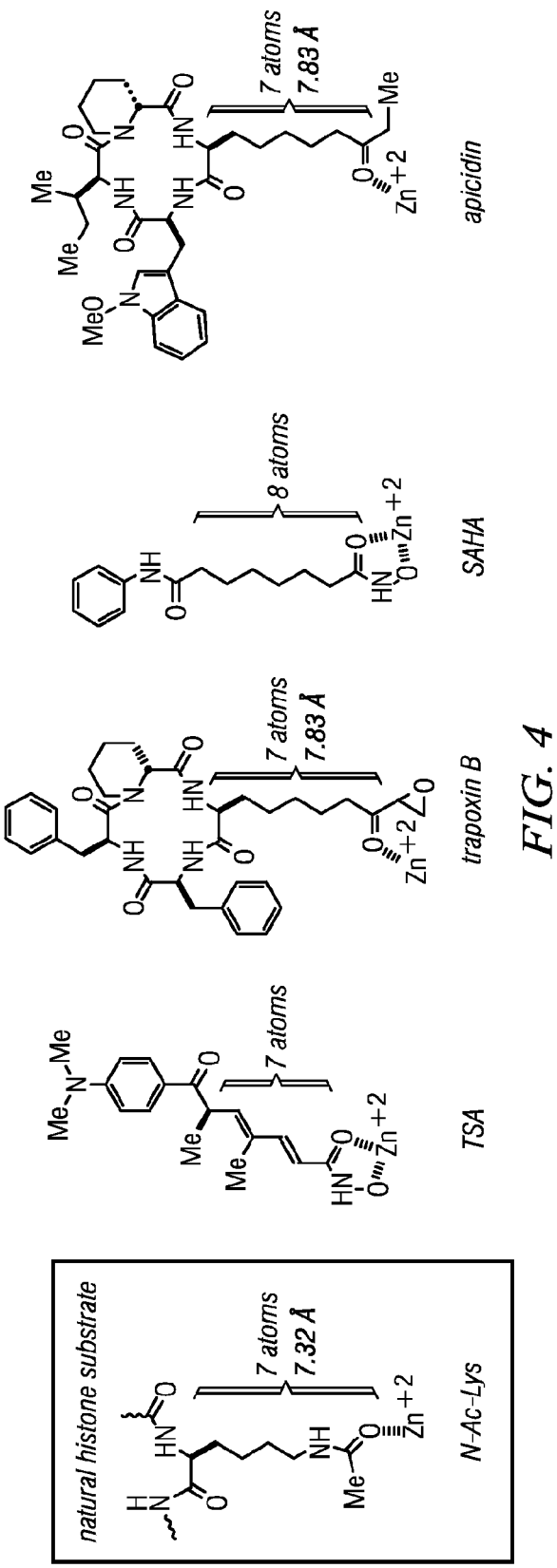
FIG. 4 illustrates one embodiment of a HDACi pharmacophore. Cap region on top; linker on the bottom with zinc-binding moiety. Figure and description adapted from (Newkirk et al. 2009).
Figure 5:
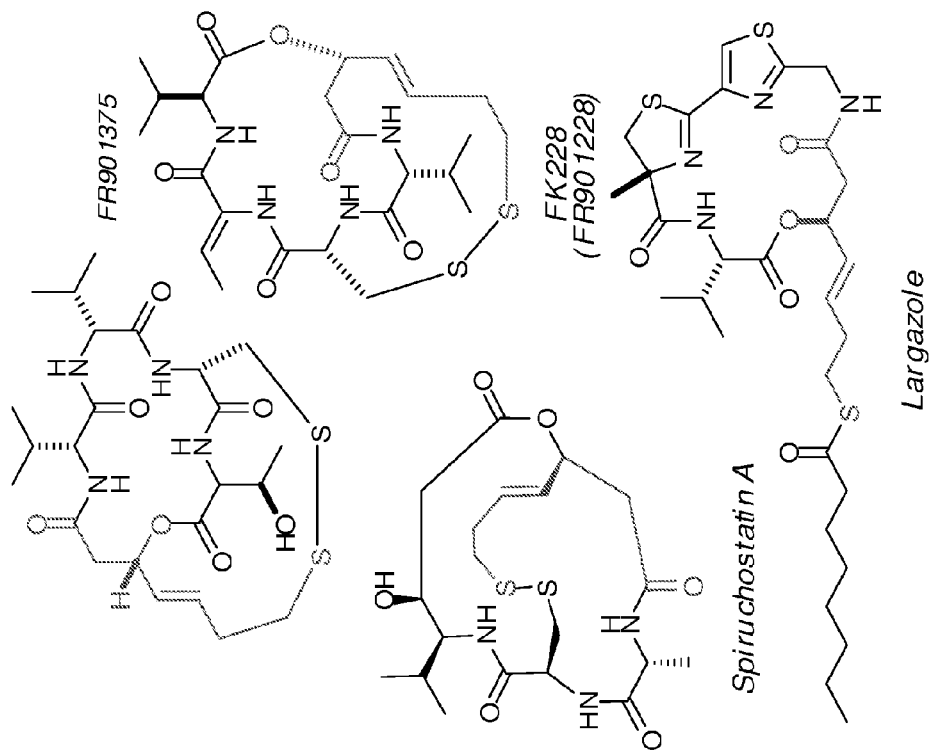
FIG. 5. Natural product depsipeptide HDAC inhibitors. The key thiol-containing domain is shown.

The structure of largazole comprises a 16-membered macrocycle containing a 4-methylthiazoline fused to a thiazole ring and an octanoic thioester side chain, a unit rarely found in natural products (Taori et al. 2008; Newkirk et al. 2009). It has been postulated that it is the macrocyclic part of the compound that interacts with the surface of the HDAC protein, while the side chain would get inserted into HDAC's active site and chelate zinc, resulting in termination of substrate deacetylation (Newkirk et al. 2009). (FIG. 4).

Figure 6:
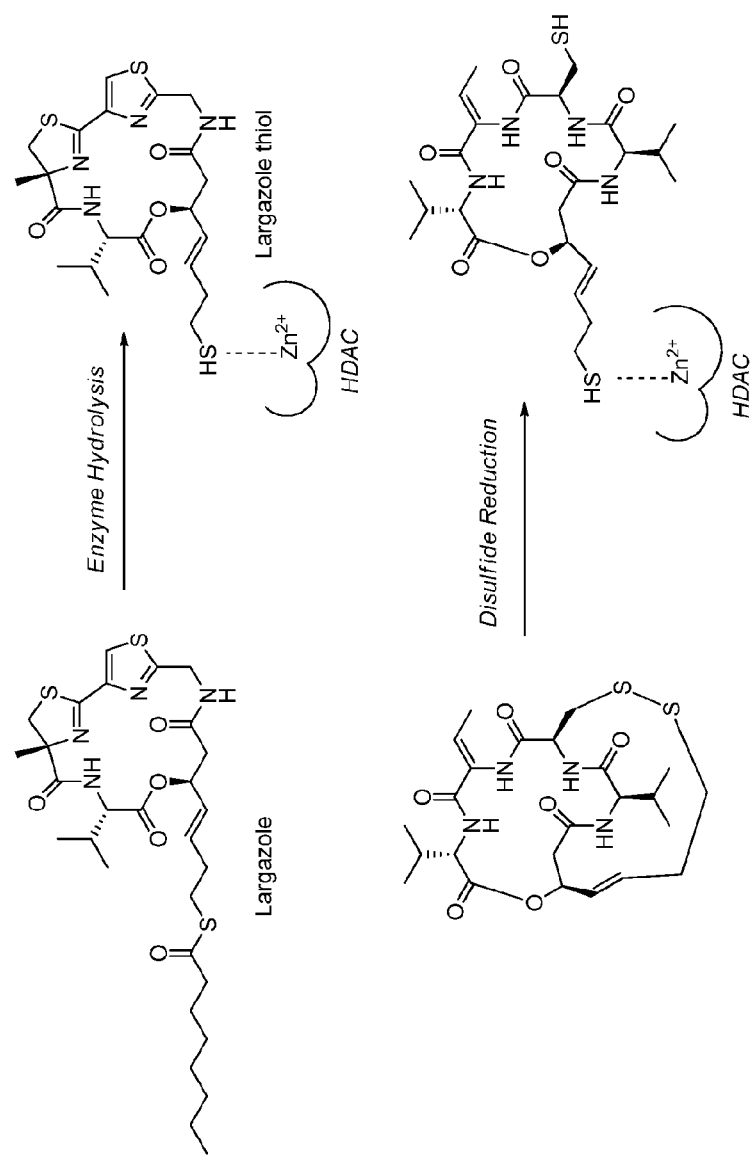
FIG. 6 depicts a possible activation of largazole and FK228 to carry out HDAC inhibition. Largazole is a prodrug that upon hydrolysis is converted to the corresponding thiol, which deactivates HDAC by chelating zinc away from the active site of the enzyme. In a similar manner, reduction of the disulfide bond in FK228 liberates thiol that potently inhibits HDACs.
Figure 7:
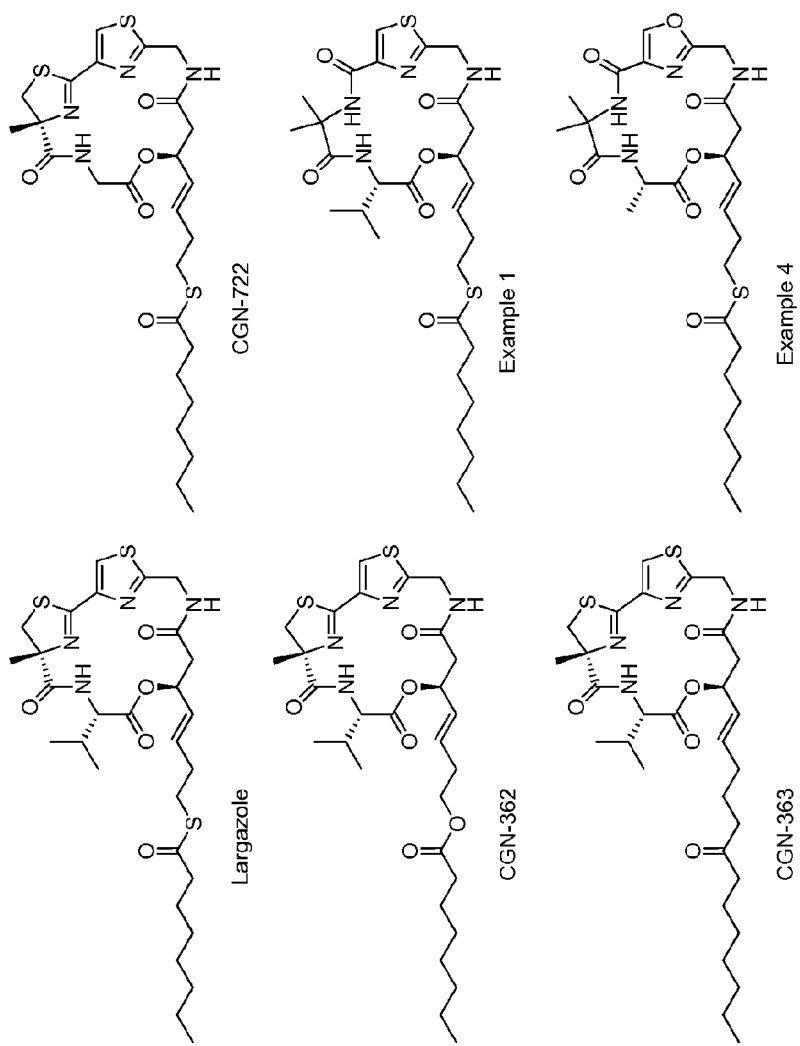
FIG. 7 provides the structures of largazole, and several structural analogues of largazole. Example 1 is also stated as CGN 552.
Figures 8A, 8B:
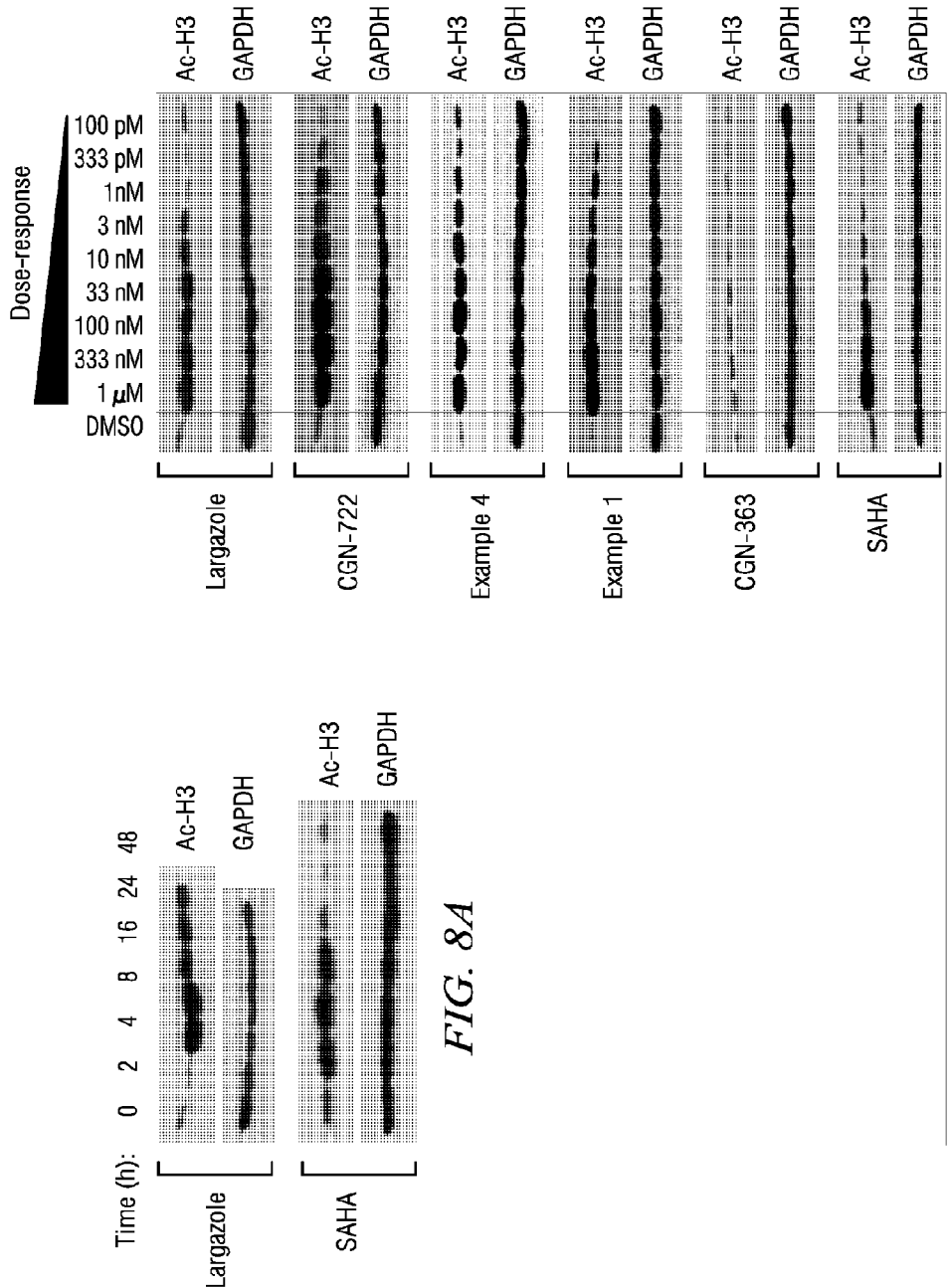
FIG. 8 presents exemplary data showing that largazole, its selected analogues, and SAHA promote H3 hyperacetylation in the HCT 116 cancer cell line.
a) Largazole (L) and SAHA inhibit H3 deacetylation in a time-dependent manner. HCT116 cells were treated with 10 nM largazole or 200 nM SAHA for the times indicated in the panel. Cell extracts were separated via SDS-PAGE electrophoresis and the resulting bands were detected utilizing anti-acetyl-H3 antibodies. DMSO-treated cells serve as a negative control, while the expression of GAPDH was used to show equal loading.

To further define largazole's pharmacophore, it stands to reason that upon its entry into the cytoplasm of the cell, the thioester moiety is rapidly hydrolyzed to produce the free thiol group, which can now interact with the zinc ion at the bottom of the HDAC pocket and potently inhibit the enzymatic activity. (FIG. 6).

To validate that largazole thiol is the reactive species, several groups synthesized a thiol derivative and assessed the biochemical potency in tumor cell growth inhibition and in cellular or in vitro HDAC inhibition assays. These findings indicate that the thiol analogue has similar HDAC inhibition using compound-treated cellular extracts (Bowers et al. 2008; Ying et al. 2008a; Ying et al. 2008b). In in vivo experiments, where cells are treated with largazole or largazole thiol, the parent molecule has higher potency with respect to HDAC inhibition ($IC_{50}$ 51 nM vs. 209 nM for the thiol metabolite) (Ying et al. 2008a).

With respect to antiproliferative activity, conflicting datasets were presented by two groups: Ying et al. show that largazole and the thiol analogue exhibit similar antigrowth activity in HCT116 cells with $GI_{50}$ values 44 and 38 nM, respectively (Ying et al. 2008b). William's group utilized a series of melanoma cell lines to demonstrate that largazole has a consistent superior potency ($IC_{50}$ 45-315 nM) compared to its thiol metabolite ($IC_{50}$ 380-2600 nM). They attributed the difference in cytotoxicity to the superior permeability of the thioester largazole (Bowers et al. 2008). To measure the deacetylase activity in vitro, purified full length HDAC proteins from class I and class II were incubated with fluorophore-conjugated substrate and largazole or largazole thiol. The results not only show that largazole itself is a much weaker HDAC inhibitor when compared to the reduced version but also indicate a pronounced preference of largazole for HDACs 1, 2, and 3 over HDAC6 (Bowers et al. 2008). To account for the lack of difference in cellular-base assays, it is possible that the thioester is cleaved under experimental conditions.

In addition, since hydroxyls do not chelate zinc, a replacement of —SH with —OH impeded the toxic effect as well as inhibitory activity in HDAC assay (Bowers et al. 2008); (Ying et al. 2008a)). Taken together, the thiol is indispensable for both activities; hence one may speculate that inhibition of HDAC promotes its antitumor effect. From a biosynthesis point of view, nature produced largazole as a prodrug rather than a target reactive species to increase its stability and to protect it from unwanted oxidation (Ying et al. 2008b). Interestingly, an analogous protect-and-liberate mechanism has been observed in a natural substance, FK228 (Shigematsu et al. 1994), (Ueda et al. 1994a; Ueda et al. 1994b). This distinctive cyclic compound contains a disulfide bond, which upon hydrolysis by glutathione reductase to butenyl thiol extends toward the zinc residue to terminate HDAC's activity. (FIG. 6; and (Furumai et al. 2002)).

A series of analogues were prepared to test the optimal length of the octanoyl chain since it is the linker that gets inserted into the HDAC pocket to chelate zinc, which results in attenuation of HDAC biological activity. It is believed that largazole as well as FK228 incorporate a four atom linker between the macrocycle and the zinc binding group. A macrocycle that lacks the entire octanoyl chain can neither inhibit HDACs nor does it have any toxic activity in cells, which further authenticates the importance of the thiol group in the role of largazole as an HDAC inhibitor. Neither shortening nor lengthening of the aliphatic chain is an advantageous structural modification as measured by in vivo and in vitro HDAC assays as well as by cell viability assay against the HCT116 colon cancer cell line. (Table 2). These results suggest that the natural length of the largazole tail is optimal (Ying et al. 2008a; Ying et al. 2008b; Newkirk et al. 2009). Furthermore, two changes within the cap region were investigated and reported by Leusch and associates: a substitution of valine to alanine and a largazole epimer (17R) (Ying et al. 2008a). The Val-, Ala compound showed a 2-fold decrease in all inhibitory activities when compared to largazole, indicating that the valine residue can be easily interchanged. An epimer analogue behaved poorly as an HDAC inhibitor, alluding to the importance of the S configuration at position C17 (Ying et al. 2008a). Recently, more structure activity relationship studies on largazole were carried out by Zeng et al (Zeng et al. 2010), where they replaced valine with leucine and phenylalanine and observed that the inhibitory activity against several cancer cell lines was slightly decreased (e.g. $GI_{50}$ for Largazole was 80 nM while 560 nM and 260 nM was measured for Leu 1 and Phe 1 respectively in HCT 116 cells). Interestingly, when valine was exchanged for tyrosine, which resulted in lowering the potency against cancer cells, it greatly increased $GI_{50}$ for normal cells, exceedingly improving the therapeutic window (HCT-116: $GI_{50}$ 0.39 µM; A549: $GI_{50}$ 1.46 µM) over the normal cell lines (HEK293:$GI_{50}$ 100 µM; HLF: $GI_{50}$ 100 µM, while largazole's $GI_{50}$ in HEK293 is 1.36 µM and 0.98 µM in HLF cells). Hence it was suggested that placing Tyr on largazole could force the compound to opt for HDACs in cancer instead of normal cells (Zeng et al. 2010).

Consequently, macrocyclic HDAC inhibitors such as largazole show potential as a tool to study the biology of HDACs while at the same time, due to largazole's preference towards killing cancer cells vs. normal cells, it holds enormous promise as a cancer therapeutic (i.e., comprises a large therapeutic window). The attractiveness of largazole also resides in the fact that it is highly selective towards the class I deacetylases, a feature rarely found in HDAC inhibitors.

In one embodiment, the present invention contemplates a method for improving upon largarzole's structure-activity relationships by creating analogs of largazole and assessing their antiproliferative effects in colon and breast cancer cell lines.

In one embodiment, the present invention provides methods for screening of compounds of present invention to determine their effect of inhibition on cancer cell growth.

In another embodiment, the present invention provides methods to increase largazole's potency and selectivity by creating a 16-member macrocycle backbone.

In yet another embodiment, the present invention provides novel analogs of largazole by breaking the ring of the 4-methylthiazoline which results in improving specificity of anti-tumor effects, for example an in vivo antitumor effect of the novel analogs are realized to a comparable efficacy relative to compounds where the 4-methylthiazoline ring is unbroken yet the number of genes impacted by the novel analog is only ⅓ of what has been changed by largazole treatment at 24 hr. This observation suggests that the novel analogs are distinct from largazole and likely have fewer side effects.

In yet another embodiment, valine of the largazole molecule was replaced within the macrocycle with an amino acid selected from the group consisting of glycine, alanine, leucine, and isoleucine.

In yet another embodiment, a valine substitution with a glycine improved the effectiveness of derivative compound by 3-fold.

In yet another embodiment of the invention, a pharmaceutical composition is provided comprising, in addition to one or more compounds described herein, at least one pharmaceutically-acceptable carrier. The composition can take any suitable form for the desired route of administration. Where the composition is to be administered orally, any suitable orally deliverable dosage form can be used, including without limitation tablets, capsules (solid or liquid filled), powders, granules, syrups and other liquids, elixirs, inhalants, troches, lozenges, and solutions. Injectable compositions or i.v. infusions are also provided in the form of solutions, suspensions, and emulsions.

In yet another embodiment, a pharmaceutical composition according to the present invention may contain one or more additional therapeutic agents, for example, to increase the efficacy or decrease side effects. In some embodiments, accordingly, a pharmaceutical composition further contains one or more additional therapeutic agents selected from active ingredients useful to treat or inhibit disease mediated directly or indirectly by HDAC. Examples of such active ingredients are, without limitation, agents to treat or inhibit cancer, Huntington's disease, cystic fibrosis, liver fibrosis, renal fibrosis, pulmonary fibrosis, skin fibrosis, rheumatoid arthritis, diabetes or heart failure.

In yet another embodiment, an additional therapeutic agent to be included is an anti-cancer agent. Examples of an anti-cancer agent include, but are not limited to, alkylating agents such as cyclophosphamide, dacarbazine, and cisplatin; anti-metabolites such as methotrexate, mercaptopurine, thioguanine, fluorouracil, and cytarabine; plant alkaloids such as vinblastine, and paclitaxel; antitumor antibiotics such as doxorubicin, bleomycin, and mitomycin; hormones/antihormones such as prednisone, tamoxifen, and flutamide; other types of anticancer agents such as asparaginase, rituximab, trastuzumab, imatinib, retinoic acid and derivatives, colony stimulating factors, amifostine, camptothecin, topotecan, thalidomide analogs such as lenalidomide, CDK inhibitors, proteasome inhibitors such as Velcade and other HDAC inhibitors.

In yet another embodiment, the present invention provides a method of inhibiting or treating diseases arising from abnormal cell proliferation and/or differentiation in a subject in need thereof, comprising administering to said subject a therapeutically effective amount of one or more compounds according to the present invention. In one embodiment, the method of inhibiting or treating disease comprises administering to a subject in need thereof, a composition comprising an effective amount of one or more compounds of the invention and a pharmaceutically acceptable carrier. The composition to be administered may further contain a therapeutic agent such as anti-cancer agent.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims. All references cited herein are incorporated in their entirety by reference.

Compounds of the Invention

The compounds of the invention are defined herein by their chemical structures and/or chemical names. The compounds of the invention are generally named according to the IUPAC or CAS nomenclature system. Abbreviations that are well known to one of ordinary skill in the art may be used. When a compound is referred to by both a chemical structure and a chemical name, and the chemical structure and chemical name conflict, the chemical structure is determinative of the compound's identity.

Compounds of Formula I of the present invention are synthesized according the generic scheme, Scheme I:

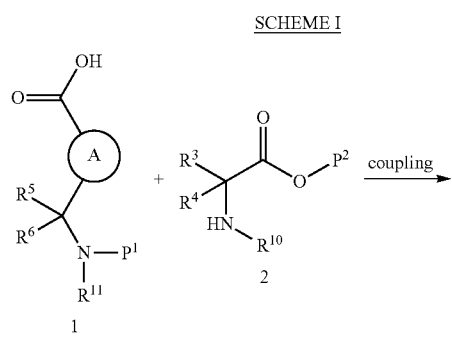

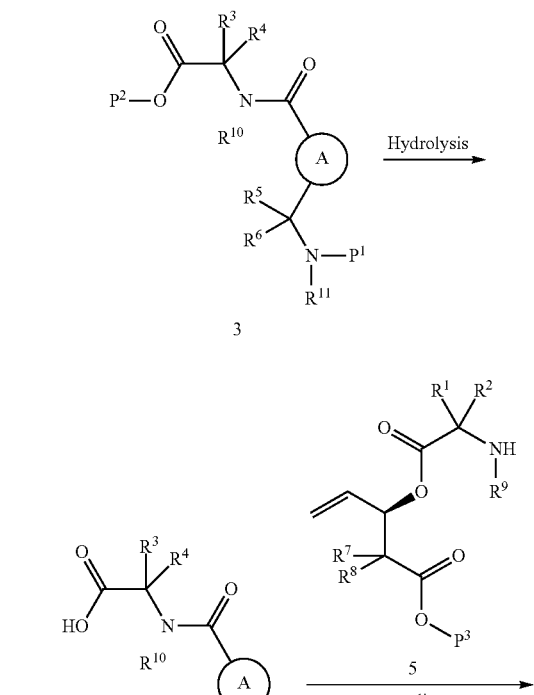

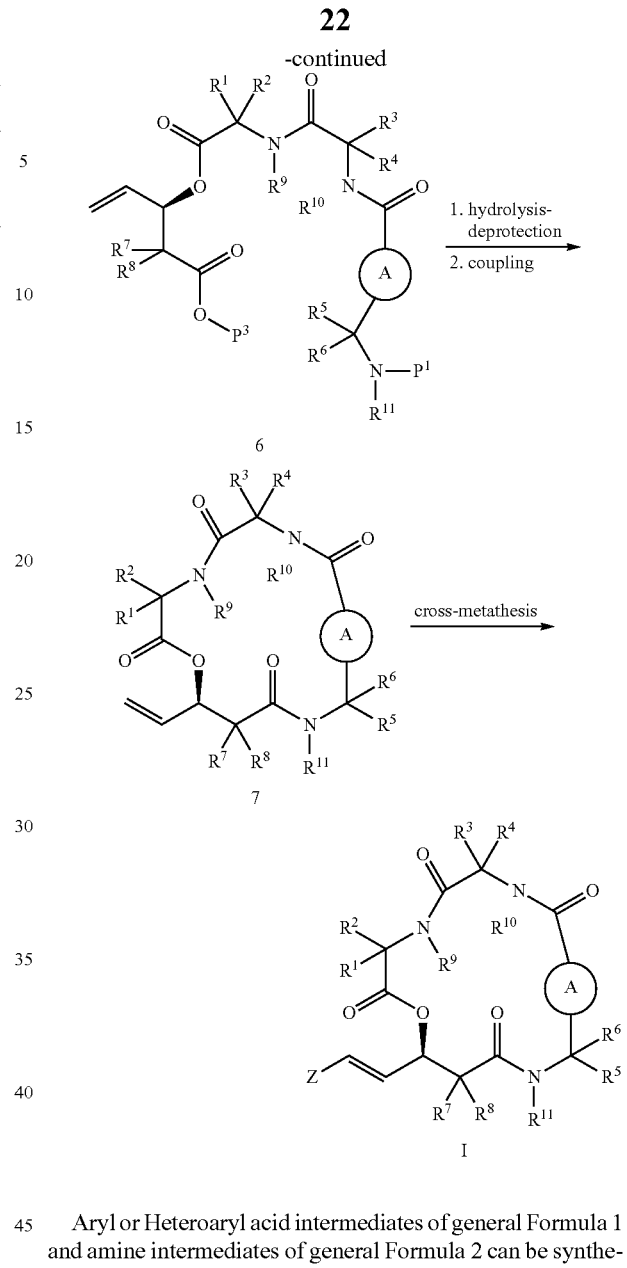

Aryl or Heteroaryl acid intermediates of general Formula 1 and amine intermediates of general Formula 2 can be synthesized by well-known methods available in the art or commercially available (Sigma-Aldrich; Advanced Chem Tech; Pep tech; Synthatech). Coupling of acids of Formula 1 and amines of Formula 2 provides amides of Formula 3, by known coupling methods using suitable reagents such as EDCI (1-ethyl-3-(3-dimethylaminopropyl)carbodiimide) or HATU (2-(7-Aza-1H-benzotriazole-1-yl)-1,1,3,3-tetramethyluronium hexafluorophosphate). Hydrolysis of the esters of Formula 3 provides acids of Formula 4, which in turn can be coupled with amines of Formula 5 to yield compounds of Formula 6. Examples of coupling agents are EDCI (1-ethyl-3-(3-dimethylaminopropyl)carbodiimide) or HATU (2-(7-Aza-1H-benzotriazole-1-yl)-1,1,3,3-tetramethyluronium hexafluorophosphate). Hydrolysis and removal of the amine protecting group of compounds of Formula 6, followed by macrocyclization provide macrolactams of general Formula 7. Macrocylzation can be achieved by reacting the deprotected amino acids of compounds of Formula 6 with diisopropyethylamine, HATU (2-(7-Aza-1H-benzotriazole-1-yl)-1,1,3,3-tetramethyluronium hexafluorophosphate) in a solvent such

EXAMPLES

The following examples are provided for illustrative purposes only and are not intended to limit the scope of the invention.

Example 1

S-(E)-4-(7S,10S)-7-isopropyl-4,4-dimethyl-2,5,8,12-tetraoxo-9-oxa-16-thia-3,6,13,18-tetraazabicyclo[13.2.1]octadeca-1(17),15 (18)-dien-10-yl)but-3-enyl octanethioate

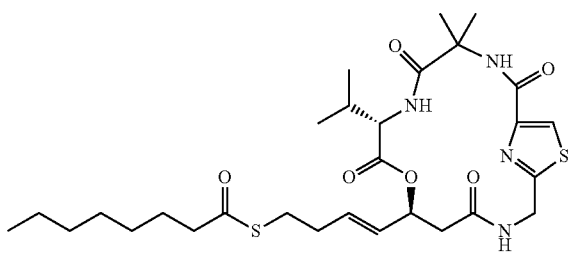 [SMILES: CCCCCCCC(=O)SCC/C=C/[C@@H]1CC(=O)NCc2nc(cs2)C(=O)NC(C)(C)C(=O)N[C@@H](C(C)C)C(=O)O1]

Step 1: Preparation of methyl 2-(2-((tert-butoxycarbonylamino)methyl)thiazole-4-carboxamido)-2-methylpropanoate To a round bottom flask with 50 mL methylene chloride was added 2-((tert-butoxycarbonylamino)methyl)thiazole-4-carboxylic acid (2.0 g, 7.74 mmole) and methyl 2-amino-2-methylpropanoate hydrochloride salt (1.25 g, 8.13 mmole). To the mixture, triethylamine (5.4 mL, 38.7 mmole) was then added, followed by 1-ethyl-3-(3-dimethylaminopropyl)carbodiimide (2.97 g, 15.5 mmole) and hydroxybenzotriazole (2.09 g, 15.5 mmole). The resulting mixture was stirred at room temperature overnight. The mixture was then diluted with methylene chloride. The mixture was then washed with water and the aqueous layer was extracted with methylene chloride. The combined organic layer was then dried over Na$_2$SO$_4$ and filtered. The filtrate was concentrated and purified by silica gel column chromatography eluting with 1:1 EtOAc/hexane to provide the desired product (2.40 g, 87% yield).

Step 2: Preparation of 2-(2-((tert-butoxycarbonylamino)methyl)thiazole-4-carboxamido)-2-methylpropanoic acid Methyl 2-(2-((tert-butoxycarbonylamino)methyl) thiazole-4-carboxamido)-2-methylpropanoate (2.4 g, 6.7 mmole) was dissolved in 10 mL methanol and 3 mL water. To the mixture, lithium hydroxide monohydrate (0.56 g, 13.4 mmole) was then added. The reaction was stirred at room temperature until TLC indicated complete consumption of starting material. To the mixture, water and EtOAc were added, and the aqueous layer was acidified with 2 N HCl to about PH 7. The layers were separated and the aqueous layer was extracted with EtOAc. The combined organic layer was dried over Na$_2$SO$_4$ and concentrated to provide the desired product as a white solid (2.3 g, quantitative yield).

Step 3: Preparation of tert-butyl (3S)-3-{[(2S)-2-(2-{[2-({[(tert-butoxy)carbonyl]amino}methyl)-1,3-thiazol-4-yl]formamido}-2-methylpropanamido)-3-methylbutanoyl]oxy}pent-4-enoate To a solution of 2-(2-((tert-butoxycarbonylamino) methyl)thiazole-4-carboxamido)-2-methylpropanoic acid (1.26 g, 3.67 mmole) in 10 mL Dimethylformamide was added HBTU(O-Benzotriazole-N,N,N',N'-tetramethyl-uronium-hexafluoro-phosphate) (1.67 g, 4.40 mmole) and diisopropylethylamine (2.0 mL, 11.0 mmole). The resulting reaction mixture was stirred at room temperature for 10 minutes. (S)-tert-butyl 3-((S)-2-amino-3-methylbutanoyloxy)pent-4-enoate (1.0 g, 3.67 mmole) was added, and the resulting mixture was stirred overnight. Water and EtOAc were added and the layers were separated. The aqueous layer was extracted with EtOAc, the combined organic layer was dried over Na$_2$SO$_4$ and concentrated. It was purified by column chromatography, eluted with 1:1 Hex/EtOAc to get the desired product (2.1 g, 96% yield).

Step 4: Preparation of (7S,10S)-7-isopropyl-4,4-dimethyl-10-vinyl-9-oxa-16-thia-3,6,13,18-tetraazabicyclo[13.2.1]octadeca-1(17),15(18)-diene-2,5,8,12-tetraone A solution of (7S,10S)-7-isopropyl-4,4-dimethyl-10-vinyl-9-oxa-16-thia-3,6,13,18-tetraazabicyclo[13.2.1]octadeca-1(17),15(18)-diene-2,5,8,12-tetraone (200 mg, 0.33 mmole) in 10 mL methylene chloride was cooled to 0° C. To the mixture, 10 mL trifluoroacetic acid was added. The mixture was stirred at 0° C. for 1.5 hours. The mixture was concentrated and azeotroped three times with toluene and one time with tetrahydrofuran to give the amine-acid. In a second round bottom flask was placed HATU (381 mg, 1.0 mmole) and N,N-diisopropylethylamine (0.51 ml, 2.85 mmole) in 70 mL tetrahydrofuran. The mixture was cooled to 0° C. The solution of the above crude amine-acid in 14 mL tetrhydrofuran was then added over 8 hours via a syringe pump. The reaction mixture was then stirred overnight in a cold room at 4° C. It was then warmed up to room temperature and stirred for 2 hours. The reaction mixture was then quenched with water. The layers were separated and the aqueous layer was extracted with EtOAc. The combined organic layer was dried over Na$_2$SO$_4$ and concentrated. The mixture was purified by silica gel chromatography, eluted with EtOAc to give the desired product. It was further purified by reverse phase chromatography, eluted with 0-100% water/CH$_3$CN to get the desired product (45 mg, 32% yield.

Step 5: Preparation of (7S,10S)-10-((E)-4-bromobut-1-enyl)-7-isopropyl-4,4-dimethyl-9-oxa-16-thia-3,6,13,18-tetraazabicyclo[13.2.1]octadeca-1(17),15(18)-diene-2,5,8,12-tetraone To a mixture of (7S,10S)-7-isopropyl-4,4-dimethyl-10-vinyl-9-oxa-16-thia-3,6,13,18-tetraazabicyclo[13.2.1]octadeca-1(17),15(18)-diene-2,5,8,12-tetraone (20 mg, 0.047 mmole) in 2 mL 1,2-dichloroethane was added 4-bromo-1-butene (25.6 mg, 0.19 mmole) and Zhan-1 catalyst (3.2 mg, 0.0047 mmole). The mixture was briefly degassed and then heated in a sealed tube at 85° C. overnight. The crude product was concentrated and passed through a silica gel plug to get a mixture of the desired product and recovered starting material (2:1 ratio). It was further purified by reversed phase chromatography, eluted with 0-80% water/CH$_3$CN to get the desired product (8 mg, 32% yield).

Step 6: Preparation of S-(E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-enyl octanethioate To a mixture of (7S,10S)-10-((E)-4-bromobut-1-enyl)-7-isopropyl-4,4-dimethyl-9-oxa-16-thia-3,6,13,18-tetraazabicyclo[13.2.1]octadeca-1(17),15(18)-diene-2,5,8,12-tetraone (15 mg, 0.028 mmole) in 1 mL acetone at room temperature was added $K_2CO_3$ (16 mg, 0.12 mmole) and octanethioic S-acid (14 mg, 0.085 mmole). The mixture was stirred at room temperature for four hours. The solvent was evaporated. The crude mixture was passed through a silica gel plug. It was further purified by reversed phase chromatography, eluted with 0-90% water/CH3CN to get the desired product (4 mg, 23% yield). $^1$H-NMR (300 MHz, $CDCl_3$) δ: 8.02 (s, 1H), 7.62 (s, 1H), 6.47 (d, J=10.85 Hz, 1H), 6.33 (dd, J=8.65, 4.50 Hz, 1H), 5.83-5.67 (m, 2H), 5.64-5.56 (m, 1H), 5.18 (dd, J=17.31, 8.22 Hz, 1H), 4.64 (dd, J=9.87, 3.97 Hz, 1H), 4.37 (dd, J=17.21, 4.01 Hz, 1H), 2.87 (t, J=7.2 Hz, 2H), 2.81-2.61 (m, 2H), 2.51 (t, J=7.5 Hz, 2H), 2.30 (m, 3H), 1.90 (s, 3H), 1.59 (m, 2H), 1.57 (s, 3H), 1.27 (m, 8H), 0.88 (m, 5H), 0.69 (d, J=6.82 Hz, 3H)

Alternative route for the Preparation of S-(E)-4-(7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-enyl octanethioate To a mixture of (7S,10S)-7-isopropyl-4,4-dimethyl-10-vinyl-9-oxa-16-thia-3,6,13,18-tetraazabicyclo[13.2.1]octadeca-1(17),15(18)-diene-2,5,8,12-tetraone (32.5 mg, 0.077 mmole, prepared from step 4) and S-but-3-enyl octanethioate (33 mg, 0.15 mmole) in 1 mL dichloroethane was added Grela catalyst (5 mg, 0.077 mmole). The mixture was purged with Argon for a few minutes and heated to 85° C. for two hours. The additional octanethioate (16.5 mg, 0.077 mmole) and Grela catalyst (5 mg, 0.077 mmole) were added. It was stirred for two more hours. The solvent was evaporated and the mixture was purified by silica gel chromatography to get the desired product (21.3 mg, 46%). MS (ESI) [M+Na$^+$]$^+$=631.3

Example 2

S-(E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15 (18)-dien-10-yl)but-3-enyl ethanethioate

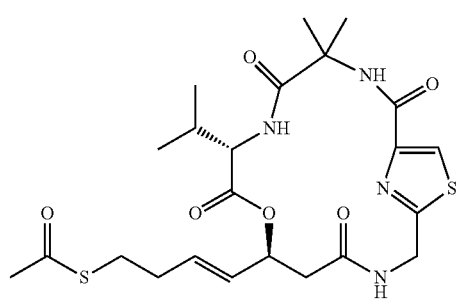 [SMILES: CC(=O)SCC/C=C/[C@@H]1CC(=O)NCc2nc(cs2)C(=O)NC(C)(C)C(=O)N[C@@H](C(C)C)C(=O)O1]

To a mixture of (7S,10S)-10-((E)-4-bromobut-1-enyl)-7-isopropyl-4,4-dimethyl-9-oxa-16-thia-3,6,13,18-tetraazabicyclo[13.2.1]octadeca-1(17),15(18)-diene-2,5,8,12-tetraone (20 mg, 0.038 mmole) (prepared as step 5 of Example 1) in 0.5 mL acetone at room temperature was added $K_2CO_3$ (10.5 mg, 0.08 mmole) and thioacetic acid (6 mg, 0.08 mmole). The mixture was stirred at room temperature for one hour. The solvent was evaporated. The crude mixture was purified by silica gel chromatograph, eluted with EtOAc, then 10% MeOH in EtOAc to get the desired product (19 mg, 96% yield). MS (ESI) [M+Na$^+$]$^+$=547.2

Example 3

S-(E)-4-(7S,10S)-7-isopropyl-2,5,8,12-tetraoxo-9-oxa-16-thia-3,6,13,18-tetraazaspiro[bicyclo[13.2.1]octadeca[1(17),15(18)]diene-4,1'-cyclopropane]-10-yl)but-3-enyl octanethioate

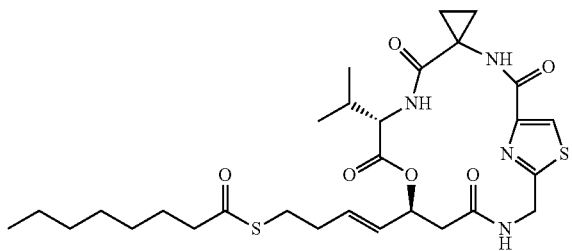 [SMILES: CCCCCCCC(=O)SCC/C=C/[C@@H]1CC(=O)NCc2nc(cs2)C(=O)NC2(CC2)C(=O)N[C@@H](C(C)C)C(=O)O1]

This compound was prepared according the procedure of Example 1 using appropriate starting materials. MS (ESI) [M+Na$^+$]$^+$=629.2

Example 4

S-(E)-4-((7S,10S)-4,4,7-trimethyl-2,5,8,12-tetraoxo-9,16-dioxa-3,6,13,18-tetraazabicyclo[13.2.1]octadeca-1(17),15(18)-dien-10-yl)but-3-enyl octanethioate

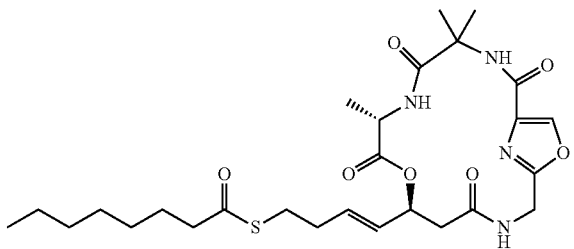 [SMILES: CCCCCCCC(=O)SCC/C=C/[C@@H]1CC(=O)NCc2nc(co2)C(=O)NC(C)(C)C(=O)N[C@@H](C)C(=O)O1]

This was prepared according the procedure of Example 1 using appropriate starting materials. MS (ESI) [M+Na$^+$]$^+$= 587.3

Example 5

(7S,10S)-4,4-dimethyl-10-[(1E)-4-(octanoylsulfanyl)but-1-en-1-yl]-7-(propan-2-yl)-9-oxa-3,6,13,19-tetraazabicyclo[13.3.1]nonadeca-1(18),15(19),16-triene-2,5,8,12-tetrone

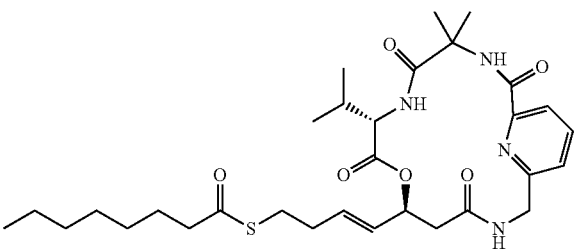 [SMILES: CCCCCCCC(=O)SCC/C=C/[C@@H]1CC(=O)NCc2cccc(n2)C(=O)NC(C)(C)C(=O)N[C@@H](C(C)C)C(=O)O1]

This was prepared according the procedure of Example 1 using appropriate starting materials. MS (ESI) [M+Na$^+$]$^+$= 625.3

Example 6

Dimer (7S,10S)-7-isopropyl-10-((E)-4-(((E)-4-(7R,10R)-7-isopropyl-4,4-dimethyl-2,5,8,12-tetraoxo-9-oxa-16-thia-3,6,13,18-tetraazabicyclo[13.2.1]octa-deca-1(17),15(18)-dien-10-yl)but-3-enyl)disulfanyl)but-1-enyl)-4,4-dimethyl-9-oxa-16-thia-3,6,13,18-tetraazabicyclo[13.2.1]octadeca-1(17),15(18)-diene-2,5,8,12-tetraone

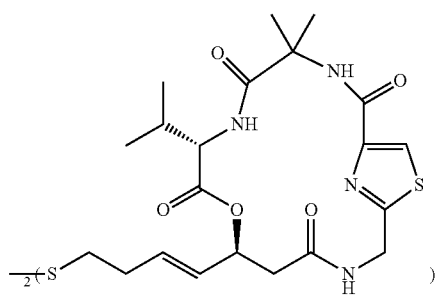

To a solution of S-(E)-4-(7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-enyl octanethioate (10 mg, 0.016 mmole) in 2 mL $CH_3CN$ was added aqueous $NH_3$(28.9%, 0.2 mL). The mixture was stirred at room temperature for 16 h. Then 0.2 mL additional aqueous ammonium was added, and the reaction was stirred for a day. Additional 0.2 mL of aqueous ammonium was added and the resulting mixture was stirred overnight. Another 0.1 mL of aqueous $NH_3$ was added and stirred for 6 hours. It was concentrated and the residue was purified by a silica gel column chromatography, eluted with EtOAc/MeOH (10/1). The fractions that contained the desired product were combined. It was purified again with reversed phase chromatography, gradient elution with 0-80% $CH_3CN$/water to get the desired product (6.5 mg, 82%). MS (ESI) $[M+Na^+]^+=985.3$ Following are few non limiting examples of compounds of Formula 1 of Scheme I:

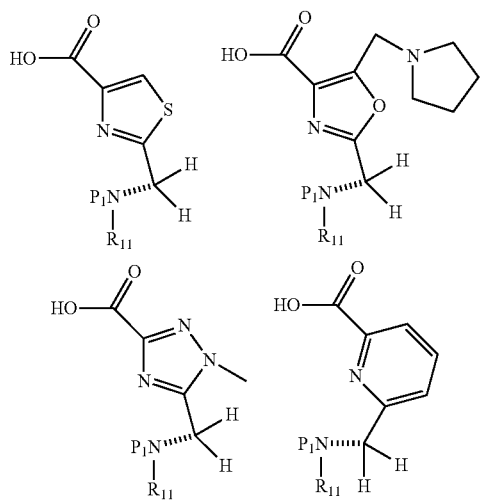

Following are few non limiting examples of compounds of Formula 2 of Scheme I:

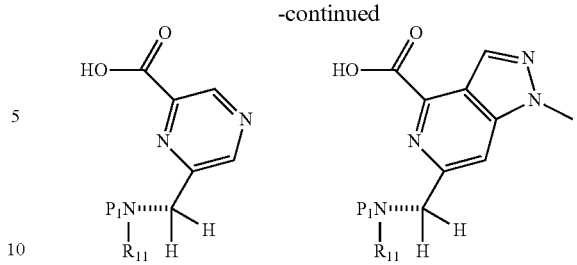

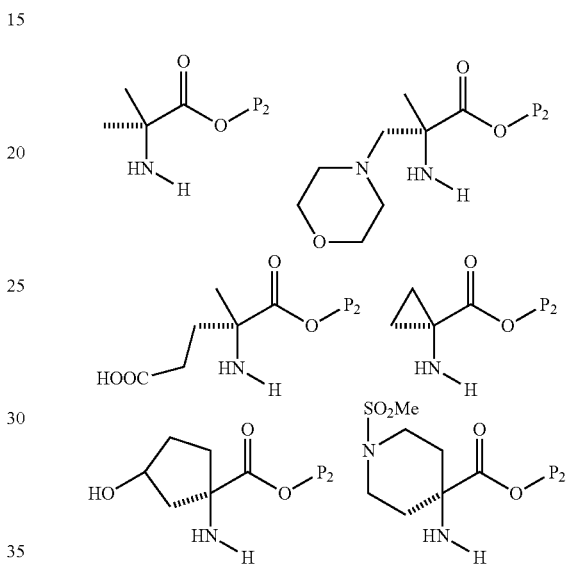

Example 7

Cell Culture

SW480, HCT116, and MDA-MB231 cell lines were purchased from the American Tissue Culture Collection. SW480 and MDA-MB231 cells were grown in Dulbecco's modified Eagle's medium supplemented with 10% fetal calf serum at 37° C. in a humidified 5% CO2 atmosphere. The HCT116 cell line was cultured in McCoy's 5a medium [ATCC; Cat. No. 30-2007] with 1.5 mM L-glutamine and 10% fetal bovine serum [ATCC; Cat. No. 30-2020]. HME cells (Clonetics, San Diego, Calif.; donor 4144) were cultured serum-free in Clonetics' recommended medium and supplements (52 µg/ml bovine pituitary extract, 0.5 µg/ml hydrocortisone, 0.01 µg/ml human epidermal growth factor, 5 µg/ml insulin, 50 µg/ml gentamicin and 50 ng/ml amphotericin-B).

Example 8

Cell Viability Assay 8,000 cells from different cancers were plated in flat-bottomed 96-well microplates. (Background control wells lacking the cells but containing the same volume of media were included in each assay plate). 24 hours after seeding, new media was added. To assess the in vitro cytotoxicity, each compound was dissolved in DMSO and prepared immediately before the experiments and was diluted into complete medium before addition to cell cultures. Test compounds were then added to the culture medium for designated decreasing concentrations (600 nM to 10 nM). Cell viability was determined 48 hours later using crystal violet dye (Sigma-Aldrich), which was solubilized in ethanol, and absorbance was measured at 588 nm using a Tecan Sail re II plate reader. Experiments were performed in replicates of six, and concentration-response curves were generated by non-linear least square regression analysis of the data using GraphPad Prism (San Diego, Calif.). The growth inhibition ($GI_{50}$) for each compound was defined as a concentration of drug leading to a 50% reduction in A588 compared with controls.

Example 9

Western Blotting

For western blot analysis, total protein extracts were prepared by lysing cells in lysis buffer (50 mM Tris-C1 [pH 8.0], 5 mM EDTA, 150 mM NaCl, 1% NP-40, 0.1% SDS, and 1 mM phenylmethylsulfonyl fluoride). 50 μg of total soluble proteins were separated by SDS-PAGE. Proteins were transferred to nitrocellulose membrane and the membrane was blocked for 1 hour with 4% nonfat milk, followed by overnight incubation at 4° C. with primary antibodies against acetylated histone H3 (1:1000, Upstate, #06-599), Ezrin (1:10000, Sigma, E-8897), Glyceraldehyde 3-phosphate dehydrogenase (GAPDH; 1:20000, Santa Cruz, sc-47724), histone H3 (H3; 1:1000, Santa Cruz, sc-8654). Membranes were then incubated with peroxidase conjugated secondary antibodies for one hour at room temperature. Detection was performed using Super Signal WestDura. The expression of Ezrin and GAPDH was used as loading control.

Example 10

Assays to Determine the Effect of Largazole and its Analogs on Cancer Cell Growth 8,000 cells from different cancer or nontransformed cells were plated in flat-bottomed 96-well microplates. (Background control wells lacking the cells but containing the same volume of media were included in each assay plate). 24 hours after seeding, new media was added. To assess the in vitro cytotoxicity, each compound was dissolved in DMSO and prepared immediately before the experiments and was diluted into complete medium before addition to cell cultures. Test compounds were then added to the culture medium for designated decreasing concentrations (600 nM to 10 nM). Cell viability was determined 48 hours later using crystal violet dye (Sigma-Aldrich), which was solubilized in ethanol, and absorbance was measured at 588 nm using a Tecan Safire II plate reader. Experiments were performed in replicates of six, and concentration-response curves were generated by non-linear least square regression analysis of the data using GraphPad Prism (San Diego, Calif.). The growth inhibition ($GI_{50}$) for each compound was defined as a concentration of drug leading to a 50% reduction in $A_{588}$ compared with controls.

Example 11

DNA Microarray Studies to Determine the Effect of SAHA, Largazole and its Analogs on Gene Expression Profiles of Cancer Cells HCT116 cells were seeded in triplicate at approximately 60% confluency. After eight hours, the cells were treated with the vehicle control DMSO (0.01%), SAHA (200 μM), Largazole (20 nM) or Example 1 (20 nM). Cells were incubated for 6 or 24 hours followed by a wash with phosphate-buffered saline. Total RNA was extracted using a RNeasy Mini RNA extraction kit (QIAGEN Inc., Valencia, Calif.) immediately after wash. Total RNA concentration was determined using a Lambda 800 UV/VIS spectrometer (PerkinElmer, Waltham, Mass.) and processed for labeling hybridization, wash, and scan at University of Colorado-Denver Health Sciences Center. Three GeneChip® Human Gene 1.0 ST (Affymetrix, Santa Clara, Calif.) arrays were used for each of the time points, cell types, and treatments for a total of 24 arrays. Expression values files for each sample were generated using the Robust Multichip Average (RMA) algorithm. Differential expression was determined using the R software package limma to generate linear models and empirical Bayesian statistics. Genes were considered differentially expressed if the P value, adjusted for multiple testing using the Benjamini and Hochberg method, was ≤5% and the log-2 fold change was ≤1 or ≥−1. GeneSpring GX (Agilent, Santa Clara, Calif.) software was used for hierarchical clustering and generating heatmaps.

REFERENCES

Allfrey, V. G., Faulkner, R., and Mirsky, A. E. 1964. Acetylation and Methylation of Histones and Their Possible Role in the Regulation of RNA Synthesis. Proc Natl Acad Sci USA 51: 786-794.

Berge, S. M., Bighley, L. D., and Monkhouse, D. C. 1977. Pharmaceutical salts. Journal of pharmaceutical sciences 66(1): 1-19.

Bowers, A., West, N., Taunton, J., Schreiber, S. L., Bradner, J. E., and Williams, R. M. 2008. Total synthesis and biological mode of action of largazole: a potent class I histone deacetylase inhibitor. J Am Chem Soc 130(33): 11219-11222.

Finnin, M. S., Donigian, J. R., Cohen, A., Richon, V. M., Rifkind, R. A., Marks, P. A., Breslow, R., and Pavletich, N. P. 1999. Structures of a histone deacetylase homologue bound to the TSA and SAHA inhibitors. Nature 401(6749): 188-193.

Furumai, R., Matsuyama, A., Kobashi, N., Lee, K.-H., Nishiyama, M., Nakajima, H., Tanaka, A., Komatsu, Y., Nishino, N., Yoshida, M., and Horinouchi, S. 2002. FK228 (depsipeptide) as a natural prodrug that inhibits class I histone deacetylases. Cancer Res 62(17): 4916-4921.

Ghosh, A. K. and Kulkarni, S. 2008. Enantioselective total synthesis of (+)-largazole, a potent inhibitor of histone deacetylase. Org Lett 10(17): 3907-3909.

Hang, H. C. and Bertozzi, C. R. 2001. Chemoselective approaches to glycoprotein assembly. Accounts of chemical research 34(9): 727-736.

Kiick, K. L., Saxon, E., Tirrell, D. A., and Bertozzi, C. R. 2002. Incorporation of azides into recombinant proteins for chemoselective modification by the Staudinger ligation. Proc Natl Acad Sci USA 99(1): 19-24.

Kim, D. H., Kim, M., and Kwon, H. J. 2003. Histone deacetylase in carcinogenesis and its inhibitors as anti-cancer agents. J Biochem Mol Biol 36(1): 110-119.

Koho, K. T. 1991. In (ed. F.P.C. Ltd).

Lane, A. A. and Chabner, B. A. 2009. Histone deacetylase inhibitors in cancer therapy. J Clin Oncol 27(32): 5459-5468.

Leder, A., Orkin, S., and Leder, P. 1975. Differentiation of erythroleukemic cells in the presence of inhibitors of DNA synthesis. Science 190(4217): 893-894.

Lemieux, G. A. and Bertozzi, C. R. 1998. Chemoselective ligation reactions with proteins, oligosaccharides and cells. Trends in biotechnology 16(12): 506-513.

Marks, P. A. 2010. The clinical development of histone deacetylase inhibitors as targeted anticancer drugs. Expert Opin Investig Drugs 19(9): 1049-1066.

Marks, P. A. and Breslow, R. 2007. Dimethyl sulfoxide to vorinostat: development of this histone deacetylase inhibitor as an anticancer drug. Nat Biotechnol 25(1): 84-90.

Masuoka, Y., Shin-Ya, K., Furihata, K., Nagai, K., Suzuki, K., Hayakawa, Y., and Seto, H. 2001. Phoenistatin, a new gene expression-enhancing substance produced by *Acremonium fusigerum*. J Antibiot (Tokyo) 54(2): 187-190.

Minucci, S, and Pelicci, P. G. 2006. Histone deacetylase inhibitors and the promise of epigenetic (and more) treatments for cancer. Nat Rev Cancer 6(1): 38-51.

Nasveschuk, C. G., Ungermannova, D., Liu, X., and Phillips, A. J. 2008. A concise total synthesis of largazole, solution structure, and some preliminary structure activity relationships. Org Lett 10(16): 3595-3598.

Newkirk, T. L., Bowers, A. A., and Williams, R. M. 2009. Discovery, biological activity, synthesis and potential therapeutic utility of naturally occurring histone deacetylase inhibitors. Nat Prod Rep 26(10): 1293-1320.

Rautio, J., Kumpulainen, H., Heimbach, T., Oliyai, R., Oh, D., Jarvinen, T., and Savolainen, J. 2008. Prodrugs: design and clinical applications. Nat Rev Drug Discov 7(3): 255-270.

Sato, T., Friend, C., and De Harven, E. 1971. Ultrastructural changes in Friend erythroleukemia cells treated with dimethyl sulfoxide. Cancer Res 31(10): 1402-1417.

Seiser, T., Kamena, F., and Cramer, N. 2008. Synthesis and biological activity of largazole and derivatives. Angew Chem Int Ed Engl 47(34): 6483-6485.

Shigematsu, N., Ueda, H., Takase, S., Tanaka, H., Yamamoto, K., and Tada, T. 1994. FR901228, a novel antitumor bicyclic depsipeptide produced by Chromobacterium violaceum No. 968. II. Structure determination. J Antibiot (Tokyo) 47(3): 311-314.

Somoza, J. R., Skene, R. J., Katz, B. A., Mol, C., Ho, J. D., Jennings, A. J., Luong, C., Arvai, A., Buggy, J. J., Chi, E., Tang, J., Sang, B.-C., Verner, E., Wynands, R., Leahy, E. M., Dougan, D. R., Snell, G., Navre, M., Knuth, M. W., Swanson, R. V., McRee, D. E., and Tari, L. W. 2004. Structural snapshots of human HDAC8 provide insights into the class I histone deacetylases. Structure 12(7): 1325-1334.

Taori, K., Paul, V. J., and Luesch, H. 2008. Structure and activity of largazole, a potent antiproliferative agent from the Floridian marine cyanobacterium Symploca sp. J Am Chem Soc 130(6): 1806-1807.

Ueda, H., Manda, T., Matsumoto, S., Mukumoto, S., Nishigaki, F., Kawamura, I., and Shimomura, K. 1994a. FR901228, a novel antitumor bicyclic depsipeptide produced by Chromobacterium violaceum No. 968. III. Antitumor activities on experimental tumors in mice. J Antibiot (Tokyo) 47(3): 315-323.

Ueda, H., Nakajima, H., Hori, Y., Goto, T., and Okuhara, M. 1994b. Action of FR901228, a novel antitumor bicyclic depsipeptide produced by Chromobacterium violaceum no. 968, on Ha-ras transformed NIH3T3 cells. Bioscience, biotechnology, and biochemistry 58(9): 1579-1583.

Ungermannova, D. 2010. P27 as a Molecular Target for Cancer Therapeutics: Discovering Small Molecule Inhibitors of P27 Proteolysis and Structure-Activity Relationship and Mechanistic Studies of Largazole, A Potent Inhibitor of Histone Deacetylase. Ph.D. thesis. University of Colorado-Boulder, Boulder, Colo., USA Vannini, A., Volpari, C., Filocamo, G., Casavola, E. C., Brunetti, M., Renzoni, D., Chakravarty, P., Paolini, C., De Francesco, R., Gallinari, P., SteinkÃ¼hler, C., and Di Marco, S. 2004. Crystal structure of a eukaryotic zinc-dependent histone deacetylase, human HDAC8, complexed with a hydroxamic acid inhibitor. Proc Natl Acad Sci USA 101(42): 15064-15069.

Manfred E. Wolff 1995. Burger's medicinal chemistry and drug discovery. 5th Edition. Volume 1: Principles and Practice. Manfred E. Wolff (ed.), Wiley-Interscience, New York. 172-178, 931-932.

Ying, Y., Liu, Y., Byeon, S. R., Kim, H., Luesch, H., and Hong, J. 2008a. Synthesis and activity of largazole analogues with linker and macrocycle modification. Org Lett 10(18): 4021-4024.

Ying, Y., Taori, K., Kim, H., Hong, J., and Luesch, H. 2008b. Total synthesis and molecular target of largazole, a histone deacetylase inhibitor. J Am Chem Soc 130(26): 8455-8459.

Zeng, X., Yin, B., Hu, Z., Liao, C., Liu, J., Li, S., Li, Z., Nicklaus, M. C., Zhou, G., and Jiang, S. Total synthesis and biological evaluation of largazole and derivatives with promising selectivity for cancers cells. Org Lett 12(6): 1368-1371.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims. All references cited herein are incorporated in their entirety by reference.

TABLE 1

| Class | Enzymes | Zn2+ Dependent | Localization | Expression |
|---|---|---|---|---|
| I | HDAC1, HDAC2, HDAC3, HDAC8 | Yes | Nucleus | Ubiquitous |
| IIa | HDAC4, HDAC5, HDAC7, HDAC9 | Yes | Nucleus and cytoplasm | Tissue specific |
| IIb | HDAC6, HDAC10 | Yes | Cytoplasm | Tissue specific |
| III | Sirtuins 1-7 | No | Variable | Variable |
| IV | HDAC11 | Yes | Nucleus and cytoplasm | Ubiquitous |

TABLE 2

Cell Growth Inhibition $GI_{50}$ in nM

| Compound (nM) | HCT-116 | Cell Lines MDA-MB231 | HME |
|---|---|---|---|
| Largazole | 28 | 71 ± 8 | 600 |
| CGN-362 | 600 | 600 | 600 |
| CGN-363 | 600 | 600 | 600 |
| CGN-722 | 9 ± 1 | 27 ± 6 | 600 |
| Example 1 | 16 ± 2 | 53 | 600 |
| Example 4 | 17 | 53 ± 3 | 600 |

TABLE 3

Summary of the Number of Genes Whose Expression Levels Changed by Two Fold Upon Treatment with Indicated Chemicals in Comparison to DMSO Control

|  | # of Genes 2 Fold-Change |
|---|---|
| Largazole @ 6 hr | 529 |
| Largazole @ 24 hr | 566 |
| Example 1 @ 6 hr | 421 |
| Example 1 @ 24 hr | 174 |
| SAHA @ 6 hr | 338 |
| SAHA @ 24 hr | 34 |
| TOTAL | 32321 |

What is claimed is:

1. A compound of Formula (I)

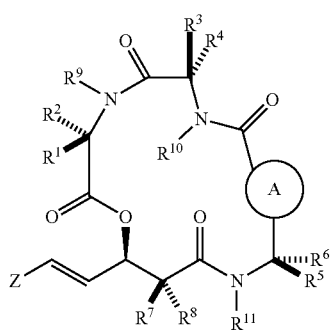

I wherein

A is aryl or heteroaryl, optionally substituted with one or more groups selected from $C_1$-$C_{10}$ alkyl, $C_3$-$C_{10}$ cycloalkyl, $C_3$-$C_{10}$ heterocycloalkyl, aryl, heteroaryl, halo, hydroxyl, —CN, —COOH, —$CF_3$, —$OCH_2F$, —$OR_{20}$, —$NR_{20}R_{22}$, —$NCOR_{20}R_{22}$ and —$CONR_{20}R_{22}$;

Z is —$(CH_2)_nSR_{12}$;

$R_1$ and $R_2$ are independently H, $C_1$-$C_{10}$ alkyl, $C_3$-$C_{10}$ cycloalkyl, $C_3$-$C_{10}$ heterocycloalkyl, or $R_1$ and $R_2$ together, or one of the $R_1$ and $R_2$ together with $R_9$ form a $C_3$-$C_{10}$ cycloalkyl or $C_3$-$C_{10}$ heterocycloalkyl, wherein the $C_1$-$C_{10}$ alkyl, $C_3$-$C_{10}$ cycloalkyl and $C_3$-$C_{10}$ heterocycloalkyl are optionally substituted with one or more groups selected from $C_1$-$C_{10}$ alkyl, $C_3$-$C_{10}$ cycloalkyl, $C_3$-$C_{10}$ heterocycloalkyl, aryl, heteroaryl, halo, hydroxyl, —CN, —COOH, —$CF_3$, —$OCH_2F$, —$OR_{20}$, —$NR_{20}R_{22}$, —$NCOR_{20}R_{22}$ and —$CONR_{20}R_{22}$;

$R_3$ and $R_4$ are independently H, $C_1$-$C_{10}$ alkyl, $C_3$-$C_{10}$ cycloalkyl, $C_3$-$C_{10}$ heterocycloalkyl, or $R_3$ and $R_4$ together, or one of the $R_3$ and $R_4$ together with $R_{10}$ form a $C_3$-$C_{10}$ cycloalkyl or $C_3$-$C_{10}$ heterocycloalkyl, wherein the $C_1$-$C_{10}$ alkyl, $C_3$-$C_{10}$ cycloalkyl and $C_3$-$C_{10}$ heterocycloalkyl are optionally substituted with one or more groups selected from $C_1$-$C_{10}$ alkyl, $C_3$-$C_{10}$ cycloalkyl, $C_3$-$C_{10}$ heterocycloalkyl, aryl, heteroaryl, halo, hydroxyl, —CN, —COOH, —$CF_3$, —$OCH_2F$, —$OR_{20}$, —$NR_{20}R_{22}$, —$NCOR_{20}R_{22}$, —$CONR_{20}R_{22}$ and —$S(O)_mR_{20}$;

$R_5$ and $R_6$ are independently H, $C_1$-$C_{10}$ alkyl, $C_3$-$C_{10}$ cycloalkyl, $C_3$-$C_{10}$ heterocycloalkyl, or $R_5$ and $R_6$ together, or one of the $R_5$ and $R_6$ together with $R_{11}$ form a $C_3$-$C_{10}$ cycloalkyl or $C_3$-$C_{10}$ heterocycloalkyl, wherein the $C_1$-$C_{10}$ alkyl, $C_3$-$C_{10}$ cycloalkyl and $C_3$-$C_{10}$ heterocycloalkyl are optionally substituted with one or more groups selected from $C_1$-$C_{10}$ alkyl, $C_3$-$C_{10}$ cycloalkyl, $C_3$-$C_{10}$ heterocycloalkyl, aryl, heteroaryl, halo, hydroxyl, —CN, —COOH, —$CF_3$, —$OCH_2F$, —$OR_{20}$, —$NR_{20}R_{22}$, —$NCOR_{20}R_{22}$ and —$CONR_{20}R_{22}$;

$R_7$ and $R_8$ are independently H, F, $C_1$-$C_{10}$ alkyl, $C_3$-$C_{10}$ cycloalkyl, $C_3$-$C_{10}$ heterocycloalkyl, or $R_7$ and $R_8$ together form a $C_3$-$C_{10}$ cycloalkyl or $C_3$-$C_{10}$ heterocycloalkyl, wherein the $C_1$-$C_{10}$ alkyl, $C_3$-$C_{10}$ cycloalkyl and $C_3$-$C_{10}$ heterocycloalkyl are optionally substituted with one or more groups selected from $C_1$-$C_{10}$ alkyl, $C_3$-$C_{10}$ cycloalkyl, $C_3$-$C_{10}$ heterocycloalkyl, aryl, heteroaryl, halo, hydroxyl, —CN, —COOH, —$CF_3$, —$OCH_2F$, —$OR_{20}$, —$NR_{20}R_{22}$, —$NCOR_{20}R_{22}$ and —$CONR_{20}R_{22}$;

$R_9$ is independently H, $C_1$-$C_{10}$ alkyl, $C_3$-$C_{10}$ cycloalkyl, $C_3$-$C_{10}$ heterocycloalkyl, or together with one of $R_1$ and $R_2$ form a $C_3$-$C_{10}$ cycloalkyl or $C_3$-$C_{10}$ heterocycloalkyl, wherein the $C_1$-$C_{10}$ alkyl, $C_3$-$C_{10}$ cycloalkyl and $C_3$-$C_{10}$ heterocycloalkyl are optionally substituted with one or more groups selected from $C_1$-$C_{10}$ alkyl, $C_3$-$C_{10}$ cycloalkyl, $C_3$-$C_{10}$ heterocycloalkyl, aryl, heteroaryl, halo, hydroxyl, —CN, —COOH, —$CF_3$, —$OCH_2F$, —$OR_{20}$, —$NR_{20}R_{22}$, —$NCOR_{20}R_{22}$ and —$CONR_{20}R_{22}$;

$R_{10}$ is independently H, $C_1$-$C_{10}$ alkyl, $C_3$-$C_{10}$ cycloalkyl, $C_3$-$C_{10}$ heterocycloalkyl, or together with one of $R_3$ and $R_4$ form a $C_3$-$C_{10}$ cycloalkyl or $C_3$-$C_{10}$ heterocycloalkyl, wherein the $C_1$-$C_{10}$ alkyl, $C_3$-$C_{10}$ cycloalkyl and $C_3$-$C_{10}$ heterocycloalkyl are optionally substituted with one or more groups selected from $C_1$-$C_{10}$ alkyl, $C_3$-$C_{10}$ cycloalkyl, $C_3$-$C_{10}$ heterocycloalkyl, aryl, heteroaryl, halo, hydroxyl, —CN, —COOH, —$CF_3$, —$OCH_2F$, —$OR_{20}$, —$NR_{20}R_{22}$, —$NCOR_{20}R_{22}$ and —$CONR_{20}R_{22}$;

$R_{11}$ is independently H, $C_1$-$C_{10}$ alkyl, $C_3$-$C_{10}$ cycloalkyl, $C_3$-$C_{10}$ heterocycloalkyl, or together with one of $R_5$ and $R_6$ form a $C_3$-$C_8$ cycloalkyl or $C_3$-$C_8$ heterocycloalkyl, wherein the $C_1$-$C_{10}$ alkyl, $C_3$-$C_{10}$ cycloalkyl and $C_3$-$C_{10}$ heterocycloalkyl are optionally substituted with one or more groups selected from $C_1$-$C_8$ alkyl, $C_3$-$C_8$ cycloalkyl, $C_3$-$C_8$ heterocycloalkyl, aryl, heteroaryl, halo, hydroxyl, —CN, —COOH, —$CF_3$, —$OCH_2F$, —$OR_{20}$, —$NR_{20}R_{22}$, —$NCOR_{20}R_{22}$ and —$CONR_{20}R_{22}$;

$R_{12}$ is independently H, $C_1$-$C_{10}$ alkyl, —$COR_{20}$, —$CONR_{20}R_{22}$, —$COOR_{20}$, —$COCR_{20}R_{22}NR_{20}R_{22}$, —$SR_{20}$, amino acid or —$P(O)(OR_{24})_2$;

$R_{20}$ and $R_{22}$ are independently H, $C_1$-$C_{10}$ alkyl, $C_3$-$C_{10}$ cycloalkyl, $C_3$-$C_{10}$ heterocycloalkyl, aryl or heteroaryl;

$R_{24}$ is independently H, $C_1$-$C_{10}$ alkyl, $C_3$-$C_{10}$ cycloalkyl, $C_3$-$C_{10}$ heterocycloalkyl, Na, K or Ca;

m=1 or 2; and n=1-6;

or a pharmaceutically acceptable salt thereof.

2. The compound according to claim 1, wherein A is a 5-membered heteroaryl ring having at least one nitrogen atom.

3. The compound according to claim 1, wherein A is a 6-membered heteroaryl ring having at least one nitrogen atom.

4. The compound according to claim 2, represented by Formula (II)

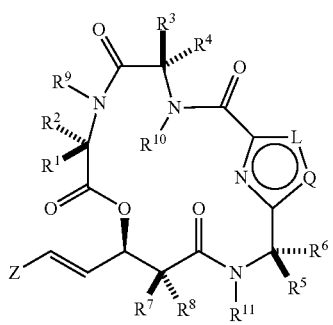

wherein
$R_1$-$R_{12}$, $R_{20}$, $R_{22}$, $R_{24}$, Z, m and n are as defined in claim 1;
L and Q are independently S, O, N, or $CR_{26}$; and
$R_{26}$ is independently H, halo, $C_1$-$C_{10}$ alkyl, $C_3$-$C_{10}$ cycloalkyl, $C_3$-$C_{10}$ heterocycloalkyl, aryl, or heteroaryl, wherein the $C_1$-$C_{10}$ alkyl, $C_3$-$C_{10}$ cycloalkyl, $C_3$-$C_{10}$ heterocycloalkyl, aryl and heteroaryl are optionally substituted with one or more groups selected from $C_1$-$C_{10}$ alkyl, $C_3$-$C_{10}$ cycloalkyl, $C_3$-$C_{10}$ heterocycloalkyl, aryl, heteroaryl, halo, hydroxyl, —CN, —COOH, —$CF_3$, —$OCH_2F$, —$OR_{20}$, —$NR_{20}R_{22}$, —$NCOR_{20}R_{22}$, and —$CONR_{20}R_{22}$;
or a pharmaceutically acceptable salt thereof.

5. The compound according to claim 2, wherein A is an oxazole or thiazole.

6. The compound according to claim 2, wherein
$R_1$ and $R_2$ are independently H, $C_1$-$C_{10}$ alkyl, $C_3$-$C_{10}$ cycloalkyl, or $R_1$ and $R_2$ together form $C_3$-$C_{10}$ cycloalkyl;
$R_3$ and $R_4$ are independently H, $C_1$-$C_{10}$ alkyl, $C_3$-$C_{10}$ cycloalkyl, or $R_3$ and $R_4$ together form $C_3$-$C_{10}$ cycloalkyl;
$R_5$ and $R_6$ are independently H, $C_1$-$C_{10}$ alkyl, $C_3$-$C_{10}$ cycloalkyl, or $R_5$ and $R_6$ together form $C_3$-$C_{10}$ cycloalkyl;
$R_7$ and $R_8$ are independently H, $C_1$-$C_{10}$ alkyl, $C_3$-$C_{10}$ cycloalkyl, or $R_5$ and $R_6$ together form $C_3$-$C_{10}$ cycloalkyl;
$R_9$, $R_{10}$ and $R_{11}$ are independently H or $C_1$-$C_{10}$ alkyl; and
$R_{12}$ is —$COR_{20}$, wherein $R_{20}$ is independently H or $C_1$-$C_{10}$ alkyl.

7. The compound according to claim 1, selected from the group consisting of:
S-(E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-enyl octanethioate;
S-(E)-4-((7S,10S)-7-isopropyl-4,4-dimethyl-2,5,8,12-tetraoxo-9-oxa-16-thia-3,6,13,18-tetraazabicyclo[13.2.1]octadeca-1(17),15(18)-dien-10-yl)but-3-enyl ethanethioate;
S-(E)-4-((7S,10S)-7-isopropyl-2,5,8,12-tetraoxo-9-oxa-16-thia-3,6,13,18-tetraazaspiro[bicyclo[13.2.1]octadeca-1[(17),15(18)]diene-4,1'-cyclopropan]-10-yl)but-3-enyl octanethioate; and
S-(E)-4-((7S,10S)-4,4,7-trimethyl-2,5,8,12-tetraoxo-9,16-dioxa-3,6,13,18-tetraazabicyclo[13.2.1]octadeca-1(17),15(18)-dien-10-yl)but-3-enyl octanethioate;
or a pharmaceutically acceptable salt thereof.

8. The compound according to claim 3, represented by Formula (III)

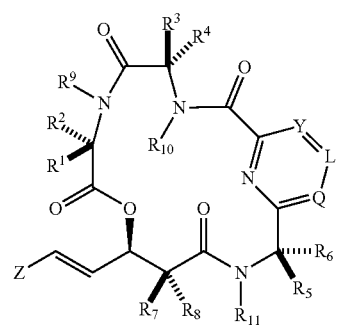

wherein
$R_1$-$R_{12}$, $R_{20}$, $R_{22}$, $R_{24}$, Z, m and n are as defined in claim 1;
L, Q and Y are independently N or $CR_{26}$; and
$R_{26}$ is independently H, halo, $C_1$-$C_{10}$ alkyl, $C_3$-$C_{10}$ cycloalkyl, $C_3$-$C_{10}$ heterocycloalkyl, aryl, or heteroaryl, wherein the $C_1$-$C_{10}$ alkyl, $C_3$-$C_{10}$ cycloalkyl, $C_3$-$C_{10}$ heterocycloalkyl, aryl and heteroaryl are optionally substituted with one or more groups selected from $C_1$-$C_{10}$ alkyl, $C_3$-$C_{10}$ cycloalkyl, $C_3$-$C_{10}$ heterocycloalkyl, aryl, heteroaryl, halo, hydroxyl, —CN, —COOH, —$CF_3$, —$OCH_2F$, —$OR_{20}$, —$NR_{20}R_{22}$, —$NCOR_{20}R_{22}$, and —$CONR_{20}R_{22}$;
or a pharmaceutically acceptable salt thereof.

9. The compound of according to claim 8, wherein
$R_1$ and $R_2$ are independently H, $C_1$-$C_{10}$ alkyl, $C_3$-$C_{10}$ cycloalkyl, or $R_1$ and $R_2$ together form a $C_3$-$C_{10}$ cycloalkyl;
$R_3$ and $R_4$ are independently H, $C_1$-$C_{10}$ alkyl, $C_3$-$C_{10}$ cycloalkyl, or $R_3$ and $R_4$ together form a $C_3$-$C_{10}$ cycloalkyl;
$R_5$ and $R_6$ are independently H, $C_1$-$C_{10}$ alkyl, $C_3$-$C_{10}$ cycloalkyl, or $R_5$ and $R_6$ together form a $C_3$-$C_{10}$ cycloalkyl;
$R_7$ and $R_8$ are independently H, $C_1$-$C_{10}$ alkyl, $C_3$-$C_{10}$ cycloalkyl, or $R_7$ and $R_8$ together form a $C_3$-$C_{10}$ cycloalkyl;
$R_9$, $R_{10}$ and $R_{11}$ are independently H or $C_1$-$C_{10}$ alkyl; and
$R_{12}$ is —$COR_{20}$, wherein $R_{20}$ is independently H or $C_1$-$C_{10}$ alkyl.

10. The compound according to claim 1, which is
(7S,10S)-4,4-dimethyl-10-[(1E)-4-(octanoylsulfanyl)but-1-en-1-yl]-7-(propan-2-yl)-9-oxa-3,6,13,19-tetraazabicyclo[13.3.1]nonadeca-1(18),15(19),16-triene-2,5,8,12-tetrone;
or a pharmaceutically acceptable salt thereof.

11. A compound of Formula (IV):

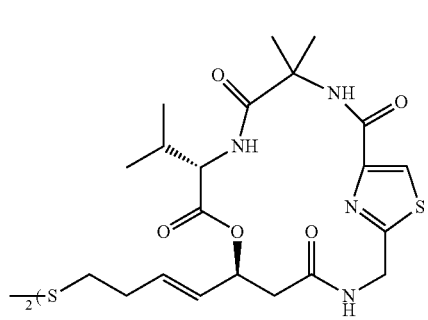

or a pharmaceutically acceptable salt thereof.

12. A pharmaceutical composition comprising a compound of claim 1 or a pharmaceutically acceptable salt thereof and a pharmaceutically acceptable carrier.

13. The pharmaceutical composition according to claim 1, further comprising one or more anti-cancer agents.

* * * * *